US012661175B2

(12) United States Patent
Yates et al.

(10) Patent No.: US 12,661,175 B2
(45) Date of Patent: *Jun. 23, 2026

(54) MEDICAL DEVICE WITH A BILATERAL JAW CONFIGURATION FOR NERVE STIMULATION

(71) Applicant: CILAG GMBH INTERNATIONAL, Zug (CH)

(72) Inventors: David C. Yates, Morrow, OH (US); Jeffrey D. Messerly, Cincinnati, OH (US); Cameron D. McLain, Fairfield, OH (US); Peter K. Shires, Robbinsville, NC (US); Frederick L. Estera, Cincinnati, OH (US); Cameron R. Nott, Fairfield, OH (US); Foster B. Stulen, Johns Island, SC (US); Christopher A. Papa, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/408,513

(22) Filed: Jan. 9, 2024

(65) Prior Publication Data

US 2024/0216042 A1 Jul. 4, 2024

Related U.S. Application Data

(63) Continuation of application No. 16/574,843, filed on Sep. 18, 2019, now Pat. No. 11,864,820, which is a
(Continued)

(51) Int. Cl.
*A61B 18/14* (2006.01)
*A61B 17/28* (2006.01)
(Continued)

(52) U.S. Cl.
CPC ...... *A61B 18/1442* (2013.01); *A61B 17/2812* (2013.01); *A61B 17/285* (2013.01);
(Continued)

(58) Field of Classification Search
CPC ............ A61B 18/1442; A61B 17/2812; A61B 17/285; A61B 17/29; A61B 17/295;
(Continued)

(56) References Cited

U.S. PATENT DOCUMENTS 969,528 A 9/1910 Disbrow
1,570,025 A 1/1926 Young
(Continued)

FOREIGN PATENT DOCUMENTS

AU 2003241752 A1 9/2003
CA 2535467 A1 4/1993
(Continued)

OTHER PUBLICATIONS

IEEE Std 802.3-2012 (Revision of IEEE Std 802.3-2008, published Dec. 28, 2012.
(Continued)

*Primary Examiner* — Eun Hwa Kim
*Assistant Examiner* — Catherine Premraj

(57) ABSTRACT

Aspects of the present disclosure are presented for a single surgical instrument configured to grasp, seal, and/or cut tissue through application of therapeutic energy, and also detect nerves through application of non-therapeutic electrical energy. A medical device may include two jaws at an end effector, used to apply therapeutic energy and to perform surgical procedures. The therapeutic energy may be in the form of ultrasonic vibrations or higher voltage electrosurgical energy. One of the jaws may be configured to cut tissue through application of the blade. In addition, one or both of the two jaws may be configured to apply nontherapeutic
(Continued)

energy for nerve stimulation probing. The application of therapeutic energy may be disabled while the nontherapeutic nerve stimulation energy is applied, and vice versa. The nontherapeutic nerve stimulation energy may be applied to the use of one or more probes positioned near one or both of the jaws.

19 Claims, 12 Drawing Sheets

Related U.S. Application Data continuation of application No. 15/493,122, filed on Apr. 20, 2017, now Pat. No. 10,456,193.

(60) Provisional application No. 62/331,123, filed on May 3, 2016.

(51) Int. Cl.

| | |
|---|---|
| *A61B 17/285* | (2006.01) |
| *A61B 17/29* | (2006.01) |
| *A61B 17/295* | (2006.01) |
| *A61B 17/32* | (2006.01) |
| *A61N 1/05* | (2006.01) |
| *A61N 1/36* | (2006.01) |
| A61B 17/00 | (2006.01) |
| A61B 18/00 | (2006.01) |
| A61B 18/12 | (2006.01) |
| A61B 18/16 | (2006.01) |
| A61N 1/04 | (2006.01) |

(52) U.S. Cl.
CPC ............ *A61B 17/29* (2013.01); *A61B 17/295* (2013.01); *A61B 17/320068* (2013.01); *A61B 17/320092* (2013.01); *A61N 1/0551* (2013.01); *A61N 1/3605* (2013.01); *A61N 1/36057* (2013.01); *A61N 1/36146* (2013.01); *A61B 2017/00017* (2013.01); *A61B 2017/2945* (2013.01); *A61B 2017/320093* (2017.08); *A61B 2017/320094* (2017.08); *A61B 2017/320095* (2017.08); *A61B 2018/00083* (2013.01); *A61B 2018/00434* (2013.01); *A61B 2018/00601* (2013.01); *A61B 2018/00607* (2013.01); *A61B 2018/0063* (2013.01); *A61B 2018/00958* (2013.01); *A61B 2018/00994* (2013.01); *A61B 2018/1253* (2013.01); *A61B 2018/126* (2013.01); *A61B 2018/162* (2013.01); *A61N 1/04* (2013.01)

(58) Field of Classification Search
CPC .... A61B 17/320068; A61B 17/320092; A61B 2017/320094; A61B 2017/320095; A61B 2017/320093; A61B 2017/00017; A61B 2017/2945; A61B 2018/00083; A61B 2018/00434; A61B 2018/00601; A61B 2018/00607; A61B 2018/0063; A61B 2018/00958; A61B 2018/00994; A61B 2018/1253; A61B 2018/126; A61B 2018/162; A61N 1/0551; A61N 1/3605; A61N 1/36057; A61N 1/36146; A61N 1/04
See application file for complete search history.

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |
| 2,597,564 | A | 5/1952 | Bugg |
| 2,704,333 | A | 3/1955 | Calosi et al. |
| 2,736,960 | A | 3/1956 | Armstrong |
| 2,748,967 | A | 6/1956 | Roach |
| 2,845,072 | A | 7/1958 | Shafer |
| 2,849,788 | A | 9/1958 | Creek |
| 2,867,039 | A | 1/1959 | Zach |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,166,971 | A | 1/1965 | Stoecker |
| 3,322,403 | A | 5/1967 | Murphy |
| 3,432,691 | A | 3/1969 | Shoh |
| 3,433,226 | A | 3/1969 | Boyd |
| 3,489,930 | A | 1/1970 | Shoh |
| 3,513,848 | A | 5/1970 | Winston et al. |
| 3,514,856 | A | 6/1970 | Camp et al. |
| 3,525,912 | A | 8/1970 | Wallin |
| 3,526,219 | A | 9/1970 | Balamuth |
| 3,554,198 | A | 1/1971 | Tatolan et al. |
| 3,580,841 | A | 5/1971 | Cadotte et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,703,651 | A | 11/1972 | Blowers |
| 3,776,238 | A | 12/1973 | Peyman et al. |
| 3,777,760 | A | 12/1973 | Essner |
| 3,805,787 | A | 4/1974 | Banko |
| 3,809,977 | A | 5/1974 | Balamuth et al. |
| 3,830,098 | A | 8/1974 | Antonevich |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,989,952 | A | 11/1976 | Hohmann |
| 4,005,714 | A | 2/1977 | Hiltebrandt |
| 4,012,647 | A | 3/1977 | Balamuth et al. |
| 4,034,762 | A | 7/1977 | Cosens et al. |
| 4,058,126 | A | 11/1977 | Leveen |
| 4,074,719 | A | 2/1978 | Semm |
| 4,156,187 | A | 5/1979 | Murry et al. |
| 4,167,944 | A | 9/1979 | Banko |
| 4,188,927 | A | 2/1980 | Harris |
| 4,200,106 | A | 4/1980 | Douvas et al. |
| 4,203,430 | A | 5/1980 | Takahashi |
| 4,203,444 | A | 5/1980 | Bonnell et al. |
| 4,220,154 | A | 9/1980 | Semm |
| 4,237,441 | A | 12/1980 | van Konynenburg et al. |
| 4,244,371 | A | 1/1981 | Farin |
| 4,281,785 | A | 8/1981 | Brooks |
| 4,300,083 | A | 11/1981 | Heiges |
| 4,302,728 | A | 11/1981 | Nakamura |
| 4,304,987 | A | 12/1981 | van Konynenburg |
| 4,306,570 | A | 12/1981 | Matthews |
| 4,314,559 | A | 2/1982 | Allen |
| 4,353,371 | A | 10/1982 | Cosman |
| 4,409,981 | A | 10/1983 | Lundberg |
| 4,445,063 | A | 4/1984 | Smith |
| 4,461,304 | A | 7/1984 | Kuperstein |
| 4,463,759 | A | 8/1984 | Garito et al. |

(56)　　　　References Cited

U.S. PATENT DOCUMENTS

| | | |
|---|---|---|
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |

(56)                References Cited

U.S. PATENT DOCUMENTS 5,318,563  A    6/1994  Malis et al.
5,318,564  A    6/1994  Eggers
5,318,570  A    6/1994  Hood et al.
5,318,589  A    6/1994  Lichtman
5,322,055  A    6/1994  Davison et al.
5,324,299  A    6/1994  Davison et al.
5,326,013  A    7/1994  Green et al.
5,326,342  A    7/1994  Pflueger et al.
5,330,471  A    7/1994  Eggers
5,330,502  A    7/1994  Hassler et al.
5,334,183  A    8/1994  Wuchinich
5,339,723  A    8/1994  Huitema
5,342,356  A    8/1994  Ellman et al.
5,342,359  A    8/1994  Rydel
5,344,420  A    9/1994  Hilal et al.
5,345,937  A    9/1994  Middleman et al.
5,346,502  A    9/1994  Estabrook et al.
5,353,474  A    10/1994  Good et al.
5,357,164  A    10/1994  Imabayashi et al.
5,357,423  A    10/1994  Weaver et al.
5,359,994  A    11/1994  Krauter et al.
5,361,583  A    11/1994  Huiterna
5,366,466  A    11/1994  Christian et al.
5,368,557  A    11/1994  Nita et al.
5,370,645  A    12/1994  Klicek et al.
5,371,429  A    12/1994  Manna
5,374,813  A    12/1994  Shipp
D354,564  S    1/1995  Medema
5,381,067  A    1/1995  Greenstein et al.
5,383,874  A    1/1995  Jackson et al.
5,383,917  A    1/1995  Desal et al.
5,387,207  A    2/1995  Dyer et al.
5,387,215  A    2/1995  Fisher
5,389,098  A    2/1995  Tsuruta et al.
5,394,187  A    2/1995  Shipp
5,395,033  A    3/1995  Byme et al.
5,395,312  A    3/1995  Desal
5,395,363  A    3/1995  Billings et al.
5,395,364  A    3/1995  Anderhub et al.
5,396,266  A    3/1995  Brimhall
5,396,900  A    3/1995  Slater et al.
5,400,267  A    3/1995  Denen et al.
5,403,312  A    4/1995  Yates et al.
5,403,334  A    4/1995  Evans et al.
5,406,503  A    4/1995  Williams, Jr. et al.
5,408,268  A    4/1995  Shipp
D358,887  S    5/1995  Feinberg
5,411,481  A    5/1995  Allen et al.
5,417,709  A    5/1995  Slater
5,419,761  A    5/1995  Narayanan et al.
5,421,829  A    6/1995  Olichney et al.
5,423,844  A    6/1995  Miller
5,428,504  A    6/1995  Bhatla
5,429,131  A    7/1995  Scheinman et al.
5,438,997  A    8/1995  Sieben et al.
5,441,499  A    8/1995  Fritzsch
5,443,463  A    8/1995  Stern et al.
5,445,638  A    8/1995  Rydell et al.
5,445,639  A    8/1995  Kuslich et al.
5,447,509  A    9/1995  Mills et al.
5,449,370  A    9/1995  Vaitekunas
5,451,053  A    9/1995  Garrido
5,451,161  A    9/1995  Sharp
5,451,220  A    9/1995  Ciervo
5,451,227  A    9/1995  Michaelson
5,456,684  A    10/1995  Schmidt et al.
5,458,598  A    10/1995  Feinberg et al.
5,462,604  A    10/1995  Shibano et al.
5,465,895  A    11/1995  Knodel et al.
5,471,988  A    12/1995  Fujio et al.
5,472,443  A    12/1995  Cordis et al.
5,476,479  A    12/1995  Green et al.
5,478,003  A    12/1995  Green et al.
5,480,409  A    1/1996  Riza
5,483,501  A    1/1996  Park et al.
5,484,436  A    1/1996  Eggers et al.
5,486,162  A    1/1996  Brumbach
5,486,189  A    1/1996  Mudry et al.
5,490,860  A    2/1996  Middle et al.
5,496,317  A    3/1996  Goble et al.
5,499,992  A    3/1996  Meade et al.
5,500,218  A    3/1996  Julian et al.
5,501,654  A    3/1996  Failla et al.
5,504,650  A    4/1996  Katsul et al.
5,505,693  A    4/1996  Mackool
5,507,297  A    4/1996  Slater et al.
5,507,738  A    4/1996  Ciervo
5,509,922  A    4/1996  Aranyi et al.
5,511,556  A    4/1996  DeSantis
5,520,704  A    5/1996  Castro et al.
5,522,832  A    6/1996  Kugo et al.
5,522,839  A    6/1996  Pilling
5,527,331  A    6/1996  Kresch et al.
5,531,744  A    7/1996  Nardella et al.
5,536,267  A    7/1996  Edwards et al.
5,540,681  A    7/1996  Strul et al.
5,540,693  A    7/1996  Fisher
5,542,916  A    8/1996  Hirsch et al.
5,548,286  A    8/1996  Craven
5,549,637  A    8/1996  Crainich
5,553,675  A    9/1996  Pitzen et al.
5,558,671  A    9/1996  Yates
5,562,609  A    10/1996  Brumbach
5,562,610  A    10/1996  Brumbach
5,562,659  A    10/1996  Morris
5,562,703  A    10/1996  Desal
5,563,179  A    10/1996  Stone et al.
5,569,164  A    10/1996  Lurz
5,571,121  A    11/1996  Heifetz
5,573,424  A    11/1996  Poppe
5,573,533  A    11/1996  Strul
5,573,534  A    11/1996  Stone
5,577,654  A    11/1996  Bishop
5,584,830  A    12/1996  Ladd et al.
5,591,187  A    1/1997  Dekel
5,593,414  A    1/1997  Shipp et al.
5,599,350  A    2/1997  Schulze et al.
5,600,526  A    2/1997  Russell et al.
5,601,601  A    2/1997  Tal et al.
5,603,773  A    2/1997  Campbell
5,607,436  A    3/1997  Pratt et al.
5,607,450  A    3/1997  Zvenyatsky et al.
5,609,573  A    3/1997  Sandock
5,611,813  A    3/1997  Lichtman
5,618,304  A    4/1997  Hart et al.
5,618,307  A    4/1997  Donlon et al.
5,618,492  A    4/1997  Auten et al.
5,620,447  A    4/1997  Smith et al.
5,624,452  A    4/1997  Yates
5,626,587  A    5/1997  Bishop et al.
5,626,595  A    5/1997  Sklar et al.
5,626,608  A    5/1997  Cuny et al.
5,628,760  A    5/1997  Knoepfler
5,630,420  A    5/1997  Vaitekunas
5,632,432  A    5/1997  Schulze et al.
5,632,717  A    5/1997  Yoon
5,640,741  A    6/1997  Yano
D381,077  S    7/1997  Hunt
5,647,871  A    7/1997  Levine et al.
5,649,937  A    7/1997  Bito et al.
5,649,955  A    7/1997  Hashimoto et al.
5,651,780  A    7/1997  Jackson et al.
5,653,713  A    8/1997  Michelson
5,655,100  A    8/1997  Ebrahim et al.
5,658,281  A    8/1997  Heard
5,662,662  A    9/1997  Bishop et al.
5,662,667  A    9/1997  Knodel
5,665,085  A    9/1997  Nardella
5,665,100  A    9/1997  Yoon
5,669,922  A    9/1997  Hood
5,674,219  A    10/1997  Monson et al.
5,674,220  A    10/1997  Fox et al.
5,674,235  A    10/1997  Paris
5,678,568  A    10/1997  Uchikubo et al.

(56)                   References Cited

U.S. PATENT DOCUMENTS

| | | |
|---|---|---|
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,928,158 A | 7/1999 | Artisides |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |

(56)　　　　References Cited

U.S. PATENT DOCUMENTS

| | | | |
|---|---|---|---|
| 6,109,500 | A | 8/2000 | Alli et al. |
| 6,110,127 | A | 8/2000 | Suzuki |
| 6,113,594 | A | 9/2000 | Savage |
| 6,113,598 | A | 9/2000 | Baker |
| 6,117,152 | A | 9/2000 | Huitema |
| H1904 | H | 10/2000 | Yates et al. |
| 6,126,629 | A | 10/2000 | Perkins |
| 6,126,658 | A | 10/2000 | Baker |
| 6,129,735 | A | 10/2000 | Okada et al. |
| 6,129,740 | A | 10/2000 | Michelson |
| 6,132,368 | A | 10/2000 | Cooper |
| 6,132,427 | A | 10/2000 | Jones et al. |
| 6,132,429 | A | 10/2000 | Baker |
| 6,132,448 | A | 10/2000 | Perez et al. |
| 6,139,320 | A | 10/2000 | Hahn |
| 6,139,561 | A | 10/2000 | Shibata et al. |
| 6,142,615 | A | 11/2000 | Qiu et al. |
| 6,142,994 | A | 11/2000 | Swanson et al. |
| 6,144,402 | A | 11/2000 | Norsworthy et al. |
| 6,147,560 | A | 11/2000 | Erhage et al. |
| 6,152,902 | A | 11/2000 | Christian et al. |
| 6,152,923 | A | 11/2000 | Ryan |
| 6,154,198 | A | 11/2000 | Rosenberg |
| 6,156,029 | A | 12/2000 | Mueller |
| 6,159,160 | A | 12/2000 | Hsei et al. |
| 6,159,175 | A | 12/2000 | Strukel et al. |
| 6,162,194 | A | 12/2000 | Shipp |
| 6,162,208 | A | 12/2000 | Hipps |
| 6,165,150 | A | 12/2000 | Banko |
| 6,174,309 | B1 | 1/2001 | Wrublewski et al. |
| 6,174,310 | B1 | 1/2001 | Kirwan, Jr. |
| 6,176,857 | B1 | 1/2001 | Ashley |
| 6,179,853 | B1 | 1/2001 | Sachse et al. |
| 6,183,426 | B1 | 2/2001 | Akisada et al. |
| 6,187,003 | B1 | 2/2001 | Buysse et al. |
| 6,190,386 | B1 | 2/2001 | Rydell |
| 6,193,709 | B1 | 2/2001 | Miyawaki et al. |
| 6,204,592 | B1 | 3/2001 | Hur |
| 6,205,383 | B1 | 3/2001 | Hermann |
| 6,205,855 | B1 | 3/2001 | Pfeiffer |
| 6,206,844 | B1 | 3/2001 | Reichel et al. |
| 6,206,876 | B1 | 3/2001 | Levine et al. |
| 6,210,337 | B1 | 4/2001 | Dunham et al. |
| 6,210,402 | B1 | 4/2001 | Olsen et al. |
| 6,210,403 | B1 | 4/2001 | Klicek |
| 6,214,023 | B1 | 4/2001 | Whipple et al. |
| 6,228,080 | B1 | 5/2001 | Gines |
| 6,231,565 | B1 | 5/2001 | Tovey et al. |
| 6,232,899 | B1 | 5/2001 | Craven |
| 6,233,476 | B1 | 5/2001 | Strommer et al. |
| 6,238,366 | B1 | 5/2001 | Savage et al. |
| 6,241,724 | B1 | 6/2001 | Fleischman et al. |
| 6,245,065 | B1 | 6/2001 | Panescu et al. |
| 6,251,110 | B1 | 6/2001 | Wampler |
| 6,252,110 | B1 | 6/2001 | Uemura et al. |
| D444,365 | S | 7/2001 | Bass et al. |
| D445,092 | S | 7/2001 | Lee |
| D445,764 | S | 7/2001 | Lee |
| 6,254,623 | B1 | 7/2001 | Haibel, Jr. et al. |
| 6,257,241 | B1 | 7/2001 | Wampler |
| 6,258,034 | B1 | 7/2001 | Hanafy |
| 6,259,230 | B1 | 7/2001 | Chou |
| 6,267,761 | B1 | 7/2001 | Ryan |
| 6,270,831 | B2 | 8/2001 | Kumar et al. |
| 6,273,852 | B1 | 8/2001 | Lehe et al. |
| 6,274,963 | B1 | 8/2001 | Estabrook et al. |
| 6,277,115 | B1 | 8/2001 | Saadat |
| 6,277,117 | B1 | 8/2001 | Tetzlaff et al. |
| 6,278,218 | B1 | 8/2001 | Madan et al. |
| 6,280,407 | B1 | 8/2001 | Manna et al. |
| 6,283,981 | B1 | 9/2001 | Beaupre |
| 6,287,344 | B1 | 9/2001 | Wampler et al. |
| 6,290,575 | B1 | 9/2001 | Shipp |
| 6,292,700 | B1 | 9/2001 | Morrison et al. |
| 6,299,591 | B1 | 10/2001 | Banko |
| 6,306,131 | B1 | 10/2001 | Hareyama et al. |
| 6,306,157 | B1 | 10/2001 | Shchervinsky |
| 6,309,400 | B2 | 10/2001 | Beaupre |
| 6,311,783 | B1 | 11/2001 | Harpell |
| 6,319,221 | B1 | 11/2001 | Savage et al. |
| 6,325,795 | B1 | 12/2001 | Lindemann et al. |
| 6,325,799 | B1 | 12/2001 | Goble |
| 6,325,811 | B1 | 12/2001 | Messerly |
| 6,328,751 | B1 | 12/2001 | Beaupre |
| 6,332,891 | B1 | 12/2001 | Himes |
| 6,338,657 | B1 | 1/2002 | Harper et al. |
| 6,340,352 | B1 | 1/2002 | Okada et al. |
| 6,340,878 | B1 | 1/2002 | Oglesbee |
| 6,350,269 | B1 | 2/2002 | Shipp et al. |
| 6,352,532 | B1 | 3/2002 | Kramer et al. |
| 6,356,224 | B1 | 3/2002 | Wohlfarth |
| 6,358,246 | B1 | 3/2002 | Behl et al. |
| 6,358,264 | B2 | 3/2002 | Banko |
| 6,364,888 | B1 | 4/2002 | Niemeyer et al. |
| 6,379,320 | B1 | 4/2002 | Lafon et al. |
| D457,958 | S | 5/2002 | Dycus et al. |
| 6,383,194 | B1 | 5/2002 | Pothula |
| 6,384,690 | B1 | 5/2002 | Wilhelmsson et al. |
| 6,387,094 | B1 | 5/2002 | Eitenmuller |
| 6,387,109 | B1 | 5/2002 | Davison et al. |
| 6,388,657 | B1 | 5/2002 | Natoll |
| 6,390,973 | B1 | 5/2002 | Ouchi |
| 6,391,026 | B1 | 5/2002 | Hung et al. |
| 6,391,042 | B1 | 5/2002 | Cimino |
| 6,398,779 | B1 | 6/2002 | Buysse et al. |
| 6,402,743 | B1 | 6/2002 | Orszulak et al. |
| 6,402,748 | B1 | 6/2002 | Schoenman et al. |
| 6,405,184 | B1 | 6/2002 | Bohme et al. |
| 6,405,733 | B1 | 6/2002 | Fogarty et al. |
| 6,409,722 | B1 | 6/2002 | Hoey et al. |
| H2037 | H | 7/2002 | Yates et al. |
| 6,416,469 | B1 | 7/2002 | Phung et al. |
| 6,416,486 | B1 | 7/2002 | Wampler |
| 6,419,675 | B1 | 7/2002 | Gallo, Sr. |
| 6,423,073 | B2 | 7/2002 | Bowman |
| 6,423,082 | B1 | 7/2002 | Houser et al. |
| 6,425,906 | B1 | 7/2002 | Young et al. |
| 6,428,538 | B1 | 8/2002 | Blewett et al. |
| 6,428,539 | B1 | 8/2002 | Baxter et al. |
| 6,430,446 | B1 | 8/2002 | Knowlton |
| 6,432,118 | B1 | 8/2002 | Messerly |
| 6,436,114 | B1 | 8/2002 | Novak et al. |
| 6,436,115 | B1 | 8/2002 | Beaupre |
| 6,440,062 | B1 | 8/2002 | Ouchi |
| 6,443,968 | B1 | 9/2002 | Holthaus et al. |
| 6,443,969 | B1 | 9/2002 | Novak et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,128 | B1 | 10/2002 | Schulze |
| 6,458,130 | B1 | 10/2002 | Frazier et al. |
| 6,458,142 | B1 | 10/2002 | Faller et al. |
| 6,459,363 | B1 | 10/2002 | Walker et al. |
| 6,461,363 | B1 | 10/2002 | Gadberry et al. |
| 6,464,689 | B1 | 10/2002 | Qin et al. |
| 6,464,702 | B2 | 10/2002 | Schulze et al. |
| 6,468,270 | B1 | 10/2002 | Hovda et al. |
| 6,475,211 | B2 | 11/2002 | Chess et al. |
| 6,475,215 | B1 | 11/2002 | Tanrisever |
| 6,480,796 | B2 | 11/2002 | Wiener |
| 6,485,490 | B2 | 11/2002 | Wampler et al. |
| 6,491,690 | B1 | 12/2002 | Goble et al. |
| 6,491,701 | B2 | 12/2002 | Tierney et al. |
| 6,491,708 | B2 | 12/2002 | Madan et al. |
| 6,497,715 | B2 | 12/2002 | Satou |
| 6,500,112 | B1 | 12/2002 | Khouri |
| 6,500,176 | B1 | 12/2002 | Truckal et al. |
| 6,500,188 | B2 | 12/2002 | Harper et al. |
| 6,500,312 | B2 | 12/2002 | Wedekamp |
| 6,503,248 | B1 | 1/2003 | Levine |
| 6,506,208 | B2 | 1/2003 | Hunt et al. |
| 6,511,478 | B1 | 1/2003 | Bumside et al. |
| 6,511,480 | B1 | 1/2003 | Tetzlaff et al. |
| 6,511,493 | B1 | 1/2003 | Moutafis et al. |

(56) References Cited

U.S. PATENT DOCUMENTS

| | | | |
|---|---|---|---|
| 6,514,252 | B2 | 2/2003 | Nezhat et al. |
| 6,514,267 | B2 | 2/2003 | Jewett |
| 6,517,565 | B1 | 2/2003 | Whitman et al. |
| 6,524,251 | B2 | 2/2003 | Rabiner et al. |
| 6,524,316 | B1 | 2/2003 | Nicholson et al. |
| 6,527,736 | B1 | 3/2003 | Attinger et al. |
| 6,531,846 | B1 | 3/2003 | Smith |
| 6,533,784 | B2 | 3/2003 | Truckal et al. |
| 6,537,272 | B2 | 3/2003 | Christopherson et al. |
| 6,537,291 | B2 | 3/2003 | Friedman et al. |
| 6,543,452 | B1 | 4/2003 | Lavigne |
| 6,543,456 | B1 | 4/2003 | Freeman |
| 6,544,260 | B1 | 4/2003 | Markel et al. |
| 6,551,309 | B1 | 4/2003 | LePivert |
| 6,554,829 | B2 | 4/2003 | Schulze et al. |
| 6,558,376 | B2 | 5/2003 | Bishop |
| 6,558,380 | B2 | 5/2003 | Lingenfelder et al. |
| 6,561,983 | B2 | 5/2003 | Cronin et al. |
| 6,562,035 | B1 | 5/2003 | Levin |
| 6,562,037 | B2 | 5/2003 | Paton et al. |
| 6,565,558 | B1 | 5/2003 | Lindenmeier et al. |
| 6,572,563 | B2 | 6/2003 | Ouchi |
| 6,572,632 | B2 | 6/2003 | Zisterer et al. |
| 6,572,639 | B1 | 6/2003 | Ingle et al. |
| 6,575,969 | B1 | 6/2003 | Rittman, III et al. |
| 6,582,427 | B1 | 6/2003 | Goble et al. |
| 6,582,451 | B1 | 6/2003 | Marucci et al. |
| 6,584,360 | B2 | 6/2003 | Francischelli et al. |
| D477,408 | S | 7/2003 | Bromley |
| 6,585,735 | B1 | 7/2003 | Frazier et al. |
| 6,588,277 | B2 | 7/2003 | Giordano et al. |
| 6,589,200 | B1 | 7/2003 | Schwemberger et al. |
| 6,589,239 | B2 | 7/2003 | Khandkar et al. |
| 6,590,733 | B1 | 7/2003 | Wilson et al. |
| 6,599,288 | B2 | 7/2003 | Maguire et al. |
| 6,602,252 | B2 | 8/2003 | Mollenauer |
| 6,602,262 | B2 | 8/2003 | Griego et al. |
| 6,607,540 | B1 | 8/2003 | Shipp |
| 6,610,059 | B1 | 8/2003 | West, Jr. |
| 6,610,060 | B2 | 8/2003 | Muller et al. |
| 6,611,793 | B1 | 8/2003 | Burnside et al. |
| 6,616,450 | B2 | 9/2003 | Mossle et al. |
| 6,619,529 | B2 | 9/2003 | Green et al. |
| 6,620,161 | B2 | 9/2003 | Schulze et al. |
| 6,622,731 | B2 | 9/2003 | Daniel et al. |
| 6,623,482 | B2 | 9/2003 | Pendekanti et al. |
| 6,623,500 | B1 | 9/2003 | Cook et al. |
| 6,623,501 | B2 | 9/2003 | Heller et al. |
| 6,626,848 | B2 | 9/2003 | Neuenfeldt |
| 6,626,926 | B2 | 9/2003 | Friedman et al. |
| 6,629,974 | B2 | 10/2003 | Penny et al. |
| 6,632,221 | B1 | 10/2003 | Edwards et al. |
| 6,633,234 | B2 | 10/2003 | Wiener et al. |
| 6,635,057 | B2 | 10/2003 | Harano et al. |
| 6,644,532 | B2 | 11/2003 | Green et al. |
| 6,651,669 | B1 | 11/2003 | Burnside |
| 6,652,513 | B2 | 11/2003 | Panescu et al. |
| 6,652,539 | B2 | 11/2003 | Shipp et al. |
| 6,652,545 | B2 | 11/2003 | Shipp et al. |
| 6,656,132 | B1 | 12/2003 | Ouchi |
| 6,656,177 | B2 | 12/2003 | Truckal et al. |
| 6,656,198 | B2 | 12/2003 | Tsonton et al. |
| 6,660,017 | B2 | 12/2003 | Beaupre |
| 6,662,127 | B2 | 12/2003 | Wiener et al. |
| 6,663,941 | B2 | 12/2003 | Brown et al. |
| 6,666,860 | B1 | 12/2003 | Takahashi |
| 6,666,875 | B1 | 12/2003 | Sakural et al. |
| 6,669,690 | B1 | 12/2003 | Okada et al. |
| 6,669,710 | B2 | 12/2003 | Moutafis et al. |
| 6,673,248 | B2 | 1/2004 | Chowdhury |
| 6,676,660 | B2 | 1/2004 | Wampler et al. |
| 6,678,621 | B2 | 1/2004 | Wiener et al. |
| 6,679,875 | B2 | 1/2004 | Honda et al. |
| 6,679,882 | B1 | 1/2004 | Kornerup |
| 6,679,899 | B2 | 1/2004 | Wiener et al. |
| 6,682,501 | B1 | 1/2004 | Nelson et al. |
| 6,682,544 | B2 | 1/2004 | Mastri et al. |
| 6,685,700 | B2 | 2/2004 | Behl et al. |
| 6,685,701 | B2 | 2/2004 | Orszulak et al. |
| 6,685,703 | B2 | 2/2004 | Pearson et al. |
| 6,689,145 | B2 | 2/2004 | Lee et al. |
| 6,689,146 | B1 | 2/2004 | Himes |
| 6,690,960 | B2 | 2/2004 | Chen et al. |
| 6,695,840 | B2 | 2/2004 | Schulze |
| 6,702,821 | B2 | 3/2004 | Bonutti |
| 6,716,215 | B1 | 4/2004 | David et al. |
| 6,719,692 | B2 | 4/2004 | Kleffner et al. |
| 6,719,765 | B2 | 4/2004 | Bonutti |
| 6,719,776 | B2 | 4/2004 | Baxter et al. |
| 6,722,552 | B2 | 4/2004 | Fenton, Jr. |
| 6,723,091 | B2 | 4/2004 | Goble et al. |
| D490,059 | S | 5/2004 | Conway et al. |
| 6,730,080 | B2 | 5/2004 | Harano et al. |
| 6,731,047 | B2 | 5/2004 | Kauf et al. |
| 6,733,498 | B2 | 5/2004 | Paton et al. |
| 6,733,506 | B1 | 5/2004 | McDevitt et al. |
| 6,736,813 | B2 | 5/2004 | Yamauchi et al. |
| 6,739,872 | B1 | 5/2004 | Turri |
| 6,740,079 | B1 | 5/2004 | Eggers et al. |
| D491,666 | S | 6/2004 | Kimmell et al. |
| 6,743,245 | B2 | 6/2004 | Lobdell |
| 6,746,284 | B1 | 6/2004 | Spink, Jr. |
| 6,746,443 | B1 | 6/2004 | Morley et al. |
| 6,752,815 | B2 | 6/2004 | Beaupre |
| 6,755,825 | B2 | 6/2004 | Shoenman et al. |
| 6,761,698 | B2 | 7/2004 | Shibata et al. |
| 6,762,535 | B2 | 7/2004 | Take et al. |
| 6,766,202 | B2 | 7/2004 | Underwood et al. |
| 6,770,072 | B1 | 8/2004 | Truckal et al. |
| 6,773,409 | B2 | 8/2004 | Truckal et al. |
| 6,773,434 | B2 | 8/2004 | Ciarrocca |
| 6,773,435 | B2 | 8/2004 | Schulze et al. |
| 6,773,443 | B2 | 8/2004 | Truwit et al. |
| 6,773,444 | B2 | 8/2004 | Messerly |
| 6,775,575 | B2 | 8/2004 | Bommannan et al. |
| 6,778,023 | B2 | 8/2004 | Christensen |
| 6,783,524 | B2 | 8/2004 | Anderson et al. |
| 6,786,382 | B1 | 9/2004 | Hoffman |
| 6,786,383 | B2 | 9/2004 | Stegelmann |
| 6,789,939 | B2 | 9/2004 | Schrodinger et al. |
| 6,790,173 | B2 | 9/2004 | Saadat et al. |
| 6,790,216 | B1 | 9/2004 | Ishikawa |
| 6,794,027 | B1 | 9/2004 | Araki et al. |
| 6,796,981 | B2 | 9/2004 | Wham et al. |
| D496,997 | S | 10/2004 | Dycus et al. |
| 6,800,085 | B2 | 10/2004 | Selmon et al. |
| 6,802,843 | B2 | 10/2004 | Truckal et al. |
| 6,808,525 | B2 | 10/2004 | Latterell et al. |
| 6,809,508 | B2 | 10/2004 | Donofrio |
| 6,810,281 | B2 | 10/2004 | Brock et al. |
| 6,811,842 | B1 | 11/2004 | Ehmsperger et al. |
| 6,814,731 | B2 | 11/2004 | Swanson |
| 6,819,027 | B2 | 11/2004 | Saraf |
| 6,821,273 | B2 | 11/2004 | Mollenauer |
| 6,827,712 | B2 | 12/2004 | Tovey et al. |
| 6,828,712 | B2 | 12/2004 | Battaglin et al. |
| 6,835,082 | B2 | 12/2004 | Gonnering |
| 6,835,199 | B2 | 12/2004 | McGuckin, Jr. et al. |
| 6,840,938 | B1 | 1/2005 | Morley et al. |
| 6,843,789 | B2 | 1/2005 | Goble |
| 6,849,073 | B2 | 2/2005 | Hoey et al. |
| 6,860,878 | B2 | 3/2005 | Brock |
| 6,860,880 | B2 | 3/2005 | Treat et al. |
| 6,863,676 | B2 | 3/2005 | Lee et al. |
| 6,866,671 | B2 | 3/2005 | Tierney et al. |
| 6,869,439 | B2 | 3/2005 | White et al. |
| 6,875,220 | B2 | 4/2005 | Du et al. |
| 6,877,647 | B2 | 4/2005 | Green et al. |
| 6,882,439 | B2 | 4/2005 | Ishijima |
| 6,887,209 | B2 | 5/2005 | Kadziauskas et al. |
| 6,887,252 | B1 | 5/2005 | Okada et al. |
| 6,893,435 | B2 | 5/2005 | Goble |
| 6,898,536 | B2 | 5/2005 | Wiener et al. |
| 6,899,685 | B2 | 5/2005 | Kermode et al. |

(56) References Cited

U.S. PATENT DOCUMENTS

| | | | |
|---|---|---|---|
| 6,905,497 B2 | 6/2005 | Truckal et al. |
| 6,908,463 B2 | 6/2005 | Treat et al. |
| 6,908,472 B2 | 6/2005 | Wiener et al. |
| 6,913,579 B2 | 7/2005 | Truckal et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckal et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckal et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckal et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckal et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckal et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckal et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckal et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckal et al. |
| 7,189,233 B2 | 3/2007 | Truckal et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckal et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |

(56) References Cited

U.S. PATENT DOCUMENTS

| | | | |
|---|---|---|---|
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckal et al. |
| 7,311,706 B2 | 12/2007 | Schoenman et al. |
| 7,311,709 B2 | 12/2007 | Truckal et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckal et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckal et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |

(56) References Cited

U.S. PATENT DOCUMENTS

| | | | |
|---|---|---|---|
| 7,674,263 | B2 | 3/2010 | Ryan |
| 7,678,069 | B1 | 3/2010 | Baker et al. |
| 7,678,105 | B2 | 3/2010 | McGreevy et al. |
| 7,678,125 | B2 | 3/2010 | Shipp |
| 7,682,366 | B2 | 3/2010 | Sakural et al. |
| 7,686,770 | B2 | 3/2010 | Cohen |
| 7,686,826 | B2 | 3/2010 | Lee et al. |
| 7,688,028 | B2 | 3/2010 | Phillips et al. |
| 7,691,095 | B2 | 4/2010 | Bednarek et al. |
| 7,691,098 | B2 | 4/2010 | Wallace et al. |
| 7,696,441 | B2 | 4/2010 | Kataoka |
| 7,699,846 | B2 | 4/2010 | Ryan |
| 7,703,459 | B2 | 4/2010 | Saadat et al. |
| 7,703,653 | B2 | 4/2010 | Shah et al. |
| 7,708,736 | B2 | 5/2010 | Chapman et al. |
| 7,708,751 | B2 | 5/2010 | Hughes et al. |
| 7,708,758 | B2 | 5/2010 | Lee et al. |
| 7,708,768 | B2 | 5/2010 | Danek et al. |
| 7,713,202 | B2 | 5/2010 | Boukhny et al. |
| 7,713,267 | B2 | 5/2010 | Pozzato |
| 7,714,481 | B2 | 5/2010 | Sakai |
| 7,717,312 | B2 | 5/2010 | Beetel |
| 7,717,914 | B2 | 5/2010 | Kimura |
| 7,717,915 | B2 | 5/2010 | Miyazawa |
| 7,721,935 | B2 | 5/2010 | Racenet et al. |
| 7,722,527 | B2 | 5/2010 | Bouchier et al. |
| 7,722,607 | B2 | 5/2010 | Dumbauld et al. |
| D618,797 | S | 6/2010 | Price et al. |
| 7,726,537 | B2 | 6/2010 | Olson et al. |
| 7,727,177 | B2 | 6/2010 | Bayat |
| 7,731,717 | B2 | 6/2010 | Odom et al. |
| 7,738,969 | B2 | 6/2010 | Bleich |
| 7,740,594 | B2 | 6/2010 | Hibner |
| 7,744,615 | B2 | 6/2010 | Couture |
| 7,749,240 | B2 | 7/2010 | Takahashi et al. |
| 7,751,115 | B2 | 7/2010 | Song |
| 7,753,245 | B2 | 7/2010 | Boudreaux et al. |
| 7,753,904 | B2 | 7/2010 | Shelton, IV et al. |
| 7,753,908 | B2 | 7/2010 | Swanson |
| 7,762,445 | B2 | 7/2010 | Heinrich et al. |
| D621,503 | S | 8/2010 | Otten et al. |
| 7,766,210 | B2 | 8/2010 | Shelton, IV et al. |
| 7,766,693 | B2 | 8/2010 | Sartor et al. |
| 7,766,910 | B2 | 8/2010 | Hixson et al. |
| 7,768,510 | B2 | 8/2010 | Tsal et al. |
| 7,770,774 | B2 | 8/2010 | Mastri et al. |
| 7,770,775 | B2 | 8/2010 | Shelton, IV et al. |
| 7,771,425 | B2 | 8/2010 | Dycus et al. |
| 7,771,444 | B2 | 8/2010 | Patel et al. |
| 7,775,972 | B2 | 8/2010 | Brock et al. |
| 7,776,036 | B2 | 8/2010 | Schechter et al. |
| 7,776,037 | B2 | 8/2010 | Odom |
| 7,778,733 | B2 | 8/2010 | Nowlin et al. |
| 7,780,054 | B2 | 8/2010 | Wales |
| 7,780,593 | B2 | 8/2010 | Ueno et al. |
| 7,780,651 | B2 | 8/2010 | Madhani et al. |
| 7,780,659 | B2 | 8/2010 | Okada et al. |
| 7,780,663 | B2 | 8/2010 | Yates et al. |
| 7,784,662 | B2 | 8/2010 | Wales et al. |
| 7,784,663 | B2 | 8/2010 | Shelton, IV |
| 7,789,883 | B2 | 9/2010 | Takashino et al. |
| 7,793,814 | B2 | 9/2010 | Racenet et al. |
| 7,794,475 | B2 | 9/2010 | Hess et al. |
| 7,796,969 | B2 | 9/2010 | Kelly et al. |
| 7,798,386 | B2 | 9/2010 | Schall et al. |
| 7,799,020 | B2 | 9/2010 | Shores et al. |
| 7,799,027 | B2 | 9/2010 | Hafner |
| 7,799,045 | B2 | 9/2010 | Masuda |
| 7,803,152 | B2 | 9/2010 | Honda et al. |
| 7,803,156 | B2 | 9/2010 | Eder et al. |
| 7,803,168 | B2 | 9/2010 | Gifford et al. |
| 7,806,891 | B2 | 10/2010 | Nowlin et al. |
| 7,810,693 | B2 | 10/2010 | Broehl et al. |
| 7,811,283 | B2 | 10/2010 | Moses et al. |
| 7,815,238 | B2 | 10/2010 | Cao |
| 7,815,641 | B2 | 10/2010 | Dodde et al. |
| 7,819,298 | B2 | 10/2010 | Hall et al. |
| 7,819,299 | B2 | 10/2010 | Shelton, IV et al. |
| 7,819,819 | B2 | 10/2010 | Quick et al. |
| 7,819,872 | B2 | 10/2010 | Johnson et al. |
| 7,821,143 | B2 | 10/2010 | Wiener |
| D627,066 | S | 11/2010 | Romero |
| 7,824,401 | B2 | 11/2010 | Manzo et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,834,484 | B2 | 11/2010 | Sartor |
| 7,837,699 | B2 | 11/2010 | Yamada et al. |
| 7,845,537 | B2 | 12/2010 | Shelton, IV et al. |
| 7,846,155 | B2 | 12/2010 | Houser et al. |
| 7,846,159 | B2 | 12/2010 | Morrison et al. |
| 7,846,160 | B2 | 12/2010 | Payne et al. |
| 7,846,161 | B2 | 12/2010 | Dumbauld et al. |
| 7,854,735 | B2 | 12/2010 | Houser et al. |
| D631,155 | S | 1/2011 | Peine et al. |
| 7,861,906 | B2 | 1/2011 | Doll et al. |
| 7,862,560 | B2 | 1/2011 | Marion |
| 7,862,561 | B2 | 1/2011 | Swanson et al. |
| 7,867,228 | B2 | 1/2011 | Nobis et al. |
| 7,871,392 | B2 | 1/2011 | Sartor |
| 7,871,423 | B2 | 1/2011 | Livneh |
| 7,876,030 | B2 | 1/2011 | Taki et al. |
| D631,965 | S | 2/2011 | Price et al. |
| 7,877,852 | B2 | 2/2011 | Unger et al. |
| 7,878,991 | B2 | 2/2011 | Babaev |
| 7,879,029 | B2 | 2/2011 | Jimenez |
| 7,879,033 | B2 | 2/2011 | Sartor et al. |
| 7,879,035 | B2 | 2/2011 | Garrison et al. |
| 7,879,070 | B2 | 2/2011 | Ortiz et al. |
| 7,883,475 | B2 | 2/2011 | Dupont et al. |
| 7,892,606 | B2 | 2/2011 | Thies et al. |
| 7,896,875 | B2 | 3/2011 | Heim et al. |
| 7,897,792 | B2 | 3/2011 | Iikura et al. |
| 7,901,400 | B2 | 3/2011 | Wham et al. |
| 7,901,423 | B2 | 3/2011 | Stulen et al. |
| 7,905,881 | B2 | 3/2011 | Masuda et al. |
| 7,909,220 | B2 | 3/2011 | Viola |
| 7,909,820 | B2 | 3/2011 | Lipson et al. |
| 7,909,824 | B2 | 3/2011 | Masuda et al. |
| 7,918,848 | B2 | 4/2011 | Lau et al. |
| 7,919,184 | B2 | 4/2011 | Mohapatra et al. |
| 7,922,061 | B2 | 4/2011 | Shelton, IV et al. |
| 7,922,651 | B2 | 4/2011 | Yamada et al. |
| 7,931,611 | B2 | 4/2011 | Novak et al. |
| 7,931,649 | B2 | 4/2011 | Couture et al. |
| D637,288 | S | 5/2011 | Houghton |
| D638,540 | S | 5/2011 | Ijiri et al. |
| 7,935,114 | B2 | 5/2011 | Takashino et al. |
| 7,936,203 | B2 | 5/2011 | Zimlich |
| 7,951,095 | B2 | 5/2011 | Makin et al. |
| 7,951,165 | B2 | 5/2011 | Golden et al. |
| 7,955,331 | B2 | 6/2011 | Truckal et al. |
| 7,956,620 | B2 | 6/2011 | Gilbert |
| 7,959,050 | B2 | 6/2011 | Smith et al. |
| 7,959,626 | B2 | 6/2011 | Hong et al. |
| 7,963,963 | B2 | 6/2011 | Francischelli et al. |
| 7,967,602 | B2 | 6/2011 | Lindquist |
| 7,972,328 | B2 | 7/2011 | Wham et al. |
| 7,972,329 | B2 | 7/2011 | Refior et al. |
| 7,976,544 | B2 | 7/2011 | McClurken et al. |
| 7,980,443 | B2 | 7/2011 | Scheib et al. |
| 7,981,050 | B2 | 7/2011 | Ritchart et al. |
| 7,981,113 | B2 | 7/2011 | Truckal et al. |
| 7,997,278 | B2 | 8/2011 | Utley et al. |
| 7,998,157 | B2 | 8/2011 | Culp et al. |
| 8,002,732 | B2 | 8/2011 | Visconti |
| 8,020,743 | B2 | 9/2011 | Shelton, IV |
| 8,025,672 | B2 | 9/2011 | Novak et al. |
| 8,028,885 | B2 | 10/2011 | Smith et al. |
| 8,033,173 | B2 | 10/2011 | Ehlert et al. |
| 8,034,049 | B2 | 10/2011 | Odom et al. |
| 8,038,693 | B2 | 10/2011 | Allen |
| 8,048,070 | B2 | 11/2011 | O'Brien et al. |
| 8,052,672 | B2 | 11/2011 | Laufer et al. |

(56) References Cited

U.S. PATENT DOCUMENTS

| | | |
|---|---|---|
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckal et al. |
| 8,075,558 B2 | 12/2011 | Truckal et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |

(56)                 References Cited

U.S. PATENT DOCUMENTS

| | | | |
|---|---|---|---|
| 8,382,792 | B2 | 2/2013 | Chojin |
| 8,388,646 | B2 | 3/2013 | Chojin |
| 8,388,647 | B2 | 3/2013 | Nau, Jr. et al. |
| 8,393,514 | B2 | 3/2013 | Shelton, IV et al. |
| 8,394,115 | B2 | 3/2013 | Houser et al. |
| 8,397,971 | B2 | 3/2013 | Yates et al. |
| 8,398,394 | B2 | 3/2013 | Sauter et al. |
| 8,403,926 | B2 | 3/2013 | Nobis et al. |
| 8,403,945 | B2 | 3/2013 | Whitfield et al. |
| 8,403,948 | B2 | 3/2013 | Deville et al. |
| 8,403,949 | B2 | 3/2013 | Palmer et al. |
| 8,403,950 | B2 | 3/2013 | Palmer et al. |
| 8,409,234 | B2 | 4/2013 | Stahler et al. |
| 8,414,577 | B2 | 4/2013 | Boudreaux et al. |
| 8,418,073 | B2 | 4/2013 | Mohr et al. |
| 8,418,349 | B2 | 4/2013 | Smith et al. |
| 8,419,757 | B2 | 4/2013 | Smith et al. |
| 8,419,758 | B2 | 4/2013 | Smith et al. |
| 8,419,759 | B2 | 4/2013 | Dietz |
| 8,423,182 | B2 | 4/2013 | Robinson et al. |
| 8,425,410 | B2 | 4/2013 | Murray et al. |
| 8,425,545 | B2 | 4/2013 | Smith et al. |
| 8,430,811 | B2 | 4/2013 | Hess et al. |
| 8,430,874 | B2 | 4/2013 | Newton et al. |
| 8,430,876 | B2 | 4/2013 | Kappus et al. |
| 8,430,897 | B2 | 4/2013 | Novak et al. |
| 8,430,898 | B2 | 4/2013 | Wiener et al. |
| 8,435,257 | B2 | 5/2013 | Smith et al. |
| 8,437,832 | B2 | 5/2013 | Govari et al. |
| 8,439,912 | B2 | 5/2013 | Cunningham et al. |
| 8,439,939 | B2 | 5/2013 | Deville et al. |
| 8,444,036 | B2 | 5/2013 | Shelton, IV |
| 8,444,637 | B2 | 5/2013 | Podmore et al. |
| 8,444,662 | B2 | 5/2013 | Palmer et al. |
| 8,444,663 | B2 | 5/2013 | Houser et al. |
| 8,444,664 | B2 | 5/2013 | Balanev et al. |
| 8,453,906 | B2 | 6/2013 | Huang et al. |
| 8,454,599 | B2 | 6/2013 | Inagaki et al. |
| 8,454,639 | B2 | 6/2013 | Du et al. |
| 8,459,525 | B2 | 6/2013 | Yates et al. |
| 8,460,284 | B2 | 6/2013 | Aronow et al. |
| 8,460,288 | B2 | 6/2013 | Tamal et al. |
| 8,460,292 | B2 | 6/2013 | Truckal et al. |
| 8,461,744 | B2 | 6/2013 | Wiener et al. |
| 8,469,981 | B2 | 6/2013 | Robertson et al. |
| 8,471,685 | B2 | 6/2013 | Shinga |
| 8,479,969 | B2 | 7/2013 | Shelton, IV |
| 8,480,703 | B2 | 7/2013 | Nicholas et al. |
| 8,484,833 | B2 | 7/2013 | Cunningham et al. |
| 8,485,413 | B2 | 7/2013 | Schelb et al. |
| 8,485,970 | B2 | 7/2013 | Widenhouse et al. |
| 8,486,057 | B2 | 7/2013 | Behnke, II |
| 8,486,096 | B2 | 7/2013 | Robertson et al. |
| 8,491,578 | B2 | 7/2013 | Manwaring et al. |
| 8,491,625 | B2 | 7/2013 | Homer |
| 8,496,682 | B2 | 7/2013 | Guerra et al. |
| D687,549 | S | 8/2013 | Johnson et al. |
| 8,506,555 | B2 | 8/2013 | Ruiz Morales |
| 8,509,318 | B2 | 8/2013 | Tailliet |
| 8,512,336 | B2 | 8/2013 | Couture |
| 8,512,337 | B2 | 8/2013 | Francischelli et al. |
| 8,512,359 | B2 | 8/2013 | Whitman et al. |
| 8,512,364 | B2 | 8/2013 | Kowalski et al. |
| 8,512,365 | B2 | 8/2013 | Wiener et al. |
| 8,518,067 | B2 | 8/2013 | Masuda et al. |
| 8,521,331 | B2 | 8/2013 | Itkowitz |
| 8,523,043 | B2 | 9/2013 | Ullrich et al. |
| 8,523,882 | B2 | 9/2013 | Huitema et al. |
| 8,523,889 | B2 | 9/2013 | Stulen et al. |
| 8,528,563 | B2 | 9/2013 | Gruber |
| 8,529,437 | B2 | 9/2013 | Taylor et al. |
| 8,529,565 | B2 | 9/2013 | Masuda et al. |
| 8,531,064 | B2 | 9/2013 | Robertson et al. |
| 8,535,308 | B2 | 9/2013 | Govari et al. |
| 8,535,311 | B2 | 9/2013 | Schall |
| 8,535,340 | B2 | 9/2013 | Allen |
| 8,535,341 | B2 | 9/2013 | Allen |
| 8,540,128 | B2 | 9/2013 | Shelton, IV et al. |
| 8,546,996 | B2 | 10/2013 | Messerly et al. |
| 8,546,999 | B2 | 10/2013 | Houser et al. |
| 8,551,077 | B2 | 10/2013 | Main et al. |
| 8,551,086 | B2 | 10/2013 | Kimura et al. |
| 8,556,929 | B2 | 10/2013 | Harper et al. |
| 8,561,870 | B2 | 10/2013 | Baxter, III et al. |
| 8,562,592 | B2 | 10/2013 | Conlon et al. |
| 8,562,598 | B2 | 10/2013 | Falkenstein et al. |
| 8,562,600 | B2 | 10/2013 | Kirkpatrick et al. |
| 8,562,604 | B2 | 10/2013 | Nishimura |
| 8,568,390 | B2 | 10/2013 | Mueller |
| 8,568,397 | B2 | 10/2013 | Horner et al. |
| 8,568,400 | B2 | 10/2013 | Gilbert |
| 8,568,412 | B2 | 10/2013 | Brandt et al. |
| 8,569,997 | B2 | 10/2013 | Lee |
| 8,573,461 | B2 | 11/2013 | Shelton, IV et al. |
| 8,573,465 | B2 | 11/2013 | Shelton, IV |
| 8,574,231 | B2 | 11/2013 | Boudreaux et al. |
| 8,574,253 | B2 | 11/2013 | Gruber et al. |
| 8,579,176 | B2 | 11/2013 | Smith et al. |
| 8,579,897 | B2 | 11/2013 | Vakharia et al. |
| 8,579,928 | B2 | 11/2013 | Robertson et al. |
| 8,579,937 | B2 | 11/2013 | Gresham |
| 8,585,727 | B2 | 11/2013 | Polo |
| 8,588,371 | B2 | 11/2013 | Ogawa et al. |
| 8,591,459 | B2 | 11/2013 | Clymer et al. |
| 8,591,506 | B2 | 11/2013 | Wham et al. |
| 8,591,536 | B2 | 11/2013 | Robertson |
| D695,407 | S | 12/2013 | Price et al. |
| D696,631 | S | 12/2013 | Price et al. |
| 8,596,513 | B2 | 12/2013 | Olson et al. |
| 8,597,193 | B2 | 12/2013 | Grunwald et al. |
| 8,597,287 | B2 | 12/2013 | Benamou et al. |
| 8,602,031 | B2 | 12/2013 | Reis et al. |
| 8,602,288 | B2 | 12/2013 | Shelton, IV et al. |
| 8,603,085 | B2 | 12/2013 | Jimenez |
| 8,603,089 | B2 | 12/2013 | Viola |
| 8,608,044 | B2 | 12/2013 | Hueil et al. |
| 8,608,045 | B2 | 12/2013 | Smith et al. |
| 8,608,745 | B2 | 12/2013 | Guzman et al. |
| 8,613,383 | B2 | 12/2013 | Beckman et al. |
| 8,616,431 | B2 | 12/2013 | Timm et al. |
| 8,617,152 | B2 | 12/2013 | Werneth et al. |
| 8,617,194 | B2 | 12/2013 | Beaupre |
| 8,622,274 | B2 | 1/2014 | Yates et al. |
| 8,623,011 | B2 | 1/2014 | Spivey |
| 8,623,016 | B2 | 1/2014 | Fischer |
| 8,623,027 | B2 | 1/2014 | Price et al. |
| 8,623,040 | B2 | 1/2014 | Artsyukhovich et al. |
| 8,623,044 | B2 | 1/2014 | Timm et al. |
| 8,628,529 | B2 | 1/2014 | Aldridge et al. |
| 8,628,534 | B2 | 1/2014 | Jones et al. |
| 8,632,461 | B2 | 1/2014 | Glossop |
| 8,636,736 | B2 | 1/2014 | Yates et al. |
| 8,638,428 | B2 | 1/2014 | Brown |
| 8,640,788 | B2 | 2/2014 | Dachs, II et al. |
| 8,641,663 | B2 | 2/2014 | Kirschenman et al. |
| 8,647,350 | B2 | 2/2014 | Mohan et al. |
| 8,650,728 | B2 | 2/2014 | Wan et al. |
| 8,652,120 | B2 | 2/2014 | Giordano et al. |
| 8,652,132 | B2 | 2/2014 | Tsuchiya et al. |
| 8,652,155 | B2 | 2/2014 | Houser et al. |
| 8,657,489 | B2 | 2/2014 | Ladurner et al. |
| 8,659,208 | B1 | 2/2014 | Rose et al. |
| 8,663,214 | B2 | 3/2014 | Weinberg et al. |
| 8,663,220 | B2 | 3/2014 | Wiener et al. |
| 8,663,222 | B2 | 3/2014 | Anderson et al. |
| 8,663,223 | B2 | 3/2014 | Masuda et al. |
| 8,663,262 | B2 | 3/2014 | Smith et al. |
| 8,668,691 | B2 | 3/2014 | Heard |
| 8,668,710 | B2 | 3/2014 | Slipszenko et al. |
| 8,684,253 | B2 | 4/2014 | Giordano et al. |
| 8,685,016 | B2 | 4/2014 | Wham et al. |
| 8,685,020 | B2 | 4/2014 | Weizman et al. |
| 8,690,582 | B2 | 4/2014 | Rohrbach et al. |
| 8,695,866 | B2 | 4/2014 | Leimbach et al. |

(56) References Cited

U.S. PATENT DOCUMENTS

| | | | |
|---|---|---|---|
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |

(56)                References Cited

U.S. PATENT DOCUMENTS

| 9,044,230 | B2 | 6/2015 | Morgan et al. |
| 9,044,238 | B2 | 6/2015 | Orszulak |
| 9,044,243 | B2 | 6/2015 | Johnson et al. |
| 9,044,245 | B2 | 6/2015 | Condie et al. |
| 9,044,256 | B2 | 6/2015 | Cadeddu et al. |
| 9,044,261 | B2 | 6/2015 | Houser |
| 9,050,083 | B2 | 6/2015 | Yates et al. |
| 9,050,093 | B2 | 6/2015 | Aldridge et al. |
| 9,050,098 | B2 | 6/2015 | Deville et al. |
| 9,050,123 | B2 | 6/2015 | Krause et al. |
| 9,050,124 | B2 | 6/2015 | Houser |
| 9,055,961 | B2 | 6/2015 | Manzo et al. |
| 9,059,547 | B2 | 6/2015 | McLawhorn |
| 9,060,770 | B2 | 6/2015 | Shelton, IV et al. |
| 9,060,775 | B2 | 6/2015 | Wiener et al. |
| 9,060,776 | B2 | 6/2015 | Yates et al. |
| 9,060,778 | B2 | 6/2015 | Condie et al. |
| 9,066,720 | B2 | 6/2015 | Ballakur et al. |
| 9,066,723 | B2 | 6/2015 | Beller et al. |
| 9,066,747 | B2 | 6/2015 | Robertson |
| 9,072,523 | B2 | 7/2015 | Houser et al. |
| 9,072,535 | B2 | 7/2015 | Shelton, IV et al. |
| 9,072,536 | B2 | 7/2015 | Shelton, IV et al. |
| 9,072,538 | B2 | 7/2015 | Suzuki et al. |
| 9,072,539 | B2 | 7/2015 | Messerly et al. |
| 9,084,624 | B2 | 7/2015 | Larkin et al. |
| 9,089,327 | B2 | 7/2015 | Worrell et al. |
| 9,089,360 | B2 | 7/2015 | Messerly et al. |
| 9,095,362 | B2 | 8/2015 | Dachs, II et al. |
| 9,095,367 | B2 | 8/2015 | Olson et al. |
| 9,099,863 | B2 | 8/2015 | Smith et al. |
| 9,101,358 | B2 | 8/2015 | Kerr et al. |
| 9,101,385 | B2 | 8/2015 | Shelton, IV et al. |
| 9,107,684 | B2 | 8/2015 | Ma |
| 9,107,689 | B2 | 8/2015 | Robertson et al. |
| 9,107,690 | B2 | 8/2015 | Bales, Jr. et al. |
| 9,113,900 | B2 | 8/2015 | Buysse et al. |
| 9,113,907 | B2 | 8/2015 | Allen, IV et al. |
| 9,113,940 | B2 | 8/2015 | Twomey |
| 9,119,657 | B2 | 9/2015 | Shelton, IV et al. |
| 9,119,957 | B2 | 9/2015 | Gantz et al. |
| 9,125,662 | B2 | 9/2015 | Shelton, IV |
| 9,125,667 | B2 | 9/2015 | Stone et al. |
| 9,144,453 | B2 | 9/2015 | Rencher et al. |
| 9,147,965 | B2 | 9/2015 | Lee |
| 9,149,324 | B2 | 10/2015 | Huang et al. |
| 9,149,325 | B2 | 10/2015 | Worrell et al. |
| 9,161,803 | B2 | 10/2015 | Yates et al. |
| 9,165,114 | B2 | 10/2015 | Jain et al. |
| 9,168,054 | B2 | 10/2015 | Turner et al. |
| 9,168,085 | B2 | 10/2015 | Juzkiw et al. |
| 9,168,089 | B2 | 10/2015 | Buysse et al. |
| 9,173,656 | B2 | 11/2015 | Schurr et al. |
| 9,179,912 | B2 | 11/2015 | Yates et al. |
| 9,186,199 | B2 | 11/2015 | Strauss et al. |
| 9,186,204 | B2 | 11/2015 | Nishimura et al. |
| 9,186,796 | B2 | 11/2015 | Ogawa |
| 9,192,380 | B2 | 11/2015 | (Tarinelli) Racenet et al. |
| 9,192,421 | B2 | 11/2015 | Garrison |
| 9,192,428 | B2 | 11/2015 | Houser et al. |
| 9,192,431 | B2 | 11/2015 | Woodruff et al. |
| 9,198,714 | B2 | 12/2015 | Worrell et al. |
| 9,198,715 | B2 | 12/2015 | Livneh |
| 9,198,718 | B2 | 12/2015 | Marczyk et al. |
| 9,198,776 | B2 | 12/2015 | Young |
| 9,204,879 | B2 | 12/2015 | Shelton, IV |
| 9,204,891 | B2 | 12/2015 | Weitzman |
| 9,204,918 | B2 | 12/2015 | Germain et al. |
| 9,204,919 | B2 | 12/2015 | Brandt et al. |
| 9,204,923 | B2 | 12/2015 | Manzo et al. |
| 9,216,050 | B2 | 12/2015 | Condie et al. |
| 9,216,051 | B2 | 12/2015 | Fischer et al. |
| 9,216,062 | B2 | 12/2015 | Duque et al. |
| 9,220,483 | B2 | 12/2015 | Frankhouser et al. |
| 9,220,527 | B2 | 12/2015 | Houser et al. |
| 9,220,559 | B2 | 12/2015 | Worrell et al. |
| 9,226,750 | B2 | 1/2016 | Weir et al. |
| 9,226,751 | B2 | 1/2016 | Shelton, IV et al. |
| 9,226,766 | B2 | 1/2016 | Aldridge et al. |
| 9,226,767 | B2 | 1/2016 | Stulen et al. |
| 9,232,979 | B2 | 1/2016 | Parihar et al. |
| 9,237,891 | B2 | 1/2016 | Shelton, IV |
| 9,237,921 | B2 | 1/2016 | Messerly et al. |
| 9,241,060 | B1 | 1/2016 | Fujisaki |
| 9,241,692 | B2 | 1/2016 | Gunday et al. |
| 9,241,728 | B2 | 1/2016 | Price et al. |
| 9,241,730 | B2 | 1/2016 | Babaev |
| 9,241,731 | B2 | 1/2016 | Boudreaux et al. |
| 9,241,768 | B2 | 1/2016 | Sandhu et al. |
| 9,247,953 | B2 | 2/2016 | Palmer et al. |
| 9,254,165 | B2 | 2/2016 | Aronow et al. |
| 9,259,234 | B2 | 2/2016 | Robertson et al. |
| 9,259,265 | B2 | 2/2016 | Harris et al. |
| 9,265,567 | B2 | 2/2016 | Orban, III et al. |
| 9,265,926 | B2 | 2/2016 | Strobl et al. |
| 9,265,973 | B2 | 2/2016 | Akagane |
| 9,277,962 | B2 | 3/2016 | Koss et al. |
| 9,282,974 | B2 | 3/2016 | Shelton, IV |
| 9,283,027 | B2 | 3/2016 | Monson et al. |
| 9,283,045 | B2 | 3/2016 | Rhee et al. |
| 9,283,054 | B2 | 3/2016 | Morgan et al. |
| 9,289,256 | B2 | 3/2016 | Shelton, IV et al. |
| 9,295,514 | B2 | 3/2016 | Shelton, IV et al. |
| 9,301,759 | B2 | 4/2016 | Spivey et al. |
| 9,305,497 | B2 | 4/2016 | Seo et al. |
| 9,307,388 | B2 | 4/2016 | Liang et al. |
| 9,307,986 | B2 | 4/2016 | Hall et al. |
| 9,308,009 | B2 | 4/2016 | Madan et al. |
| 9,308,014 | B2 | 4/2016 | Fischer |
| 9,314,261 | B2 | 4/2016 | Bales, Jr. et al. |
| 9,314,292 | B2 | 4/2016 | Trees et al. |
| 9,314,301 | B2 | 4/2016 | Ben-Haim et al. |
| 9,326,754 | B2 | 5/2016 | Polster |
| 9,326,767 | B2 | 5/2016 | Koch et al. |
| 9,326,787 | B2 | 5/2016 | Sanal et al. |
| 9,326,788 | B2 | 5/2016 | Batross et al. |
| 9,332,987 | B2 | 5/2016 | Leimbach et al. |
| 9,333,025 | B2 | 5/2016 | Monson et al. |
| 9,333,034 | B2 | 5/2016 | Hancock |
| 9,339,289 | B2 | 5/2016 | Robertson |
| 9,339,323 | B2 | 5/2016 | Eder et al. |
| 9,339,326 | B2 | 5/2016 | McCullagh et al. |
| 9,345,481 | B2 | 5/2016 | Hall et al. |
| 9,345,534 | B2 | 5/2016 | Artale et al. |
| 9,345,900 | B2 | 5/2016 | Wu et al. |
| 9,351,642 | B2 | 5/2016 | Nadkarni et al. |
| 9,351,726 | B2 | 5/2016 | Leimbach et al. |
| 9,351,727 | B2 | 5/2016 | Leimbach et al. |
| 9,351,754 | B2 | 5/2016 | Vakharia et al. |
| 9,352,173 | B2 | 5/2016 | Yamada et al. |
| 9,358,003 | B2 | 6/2016 | Hall et al. |
| 9,358,065 | B2 | 6/2016 | Ladtkow et al. |
| 9,364,171 | B2 | 6/2016 | Harris et al. |
| 9,364,230 | B2 | 6/2016 | Shelton, IV et al. |
| 9,364,279 | B2 | 6/2016 | Houser et al. |
| 9,370,364 | B2 | 6/2016 | Smith et al. |
| 9,370,400 | B2 | 6/2016 | Parihar |
| 9,370,611 | B2 | 6/2016 | Ross et al. |
| 9,375,230 | B2 | 6/2016 | Ross et al. |
| 9,375,232 | B2 | 6/2016 | Hunt et al. |
| 9,375,256 | B2 | 6/2016 | Cunningham et al. |
| 9,375,264 | B2 | 6/2016 | Horner et al. |
| 9,375,267 | B2 | 6/2016 | Kerr et al. |
| 9,385,831 | B2 | 7/2016 | Marr et al. |
| 9,386,983 | B2 | 7/2016 | Swensgard et al. |
| 9,393,037 | B2 | 7/2016 | Olson et al. |
| 9,393,070 | B2 | 7/2016 | Gelfand et al. |
| 9,398,911 | B2 | 7/2016 | Auld |
| 9,402,680 | B2 | 8/2016 | Ginnebaugh et al. |
| 9,402,682 | B2 | 8/2016 | Worrell et al. |
| 9,408,606 | B2 | 8/2016 | Shelton, IV |
| 9,408,622 | B2 | 8/2016 | Stulen et al. |
| 9,408,660 | B2 | 8/2016 | Strobl et al. |
| 9,414,853 | B2 | 8/2016 | Stulen et al. |

(56) References Cited

U.S. PATENT DOCUMENTS

| | | | |
|---|---|---|---|
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behrike, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,128 B2 | 9/2017 | Baber et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,826,977 B2 | 11/2017 | Leimbach et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,860 B2 | 2/2018 | Leimbach |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,901,321 B2 | 2/2018 | Harks et al. |

(56) References Cited

U.S. PATENT DOCUMENTS

| | | |
|---|---|---|
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |

(56) References Cited

U.S. PATENT DOCUMENTS

| | | | |
|---|---|---|---|
| 10,398,466 | B2 | 9/2019 | Stulen et al. |
| 10,398,497 | B2 | 9/2019 | Batross et al. |
| 10,405,857 | B2 | 9/2019 | Shelton, IV et al. |
| 10,405,863 | B2 | 9/2019 | Wise et al. |
| 10,413,291 | B2 | 9/2019 | Worthington et al. |
| 10,413,293 | B2 | 9/2019 | Shelton, IV et al. |
| 10,413,297 | B2 | 9/2019 | Harris et al. |
| 10,413,352 | B2 | 9/2019 | Thomas et al. |
| 10,413,353 | B2 | 9/2019 | Kerr et al. |
| 10,420,552 | B2 | 9/2019 | Shelton, IV et al. |
| 10,420,579 | B2 | 9/2019 | Wiener et al. |
| 10,420,607 | B2 | 9/2019 | Woloszko et al. |
| D865,175 | S | 10/2019 | Widenhouse et al. |
| 10,426,471 | B2 | 10/2019 | Shelton, IV et al. |
| 10,426,507 | B2 | 10/2019 | Wiener et al. |
| 10,426,978 | B2 | 10/2019 | Akagane |
| 10,433,837 | B2 | 10/2019 | Worthington et al. |
| 10,433,849 | B2 | 10/2019 | Shelton, IV et al. |
| 10,433,865 | B2 | 10/2019 | Witt et al. |
| 10,433,866 | B2 | 10/2019 | Witt et al. |
| 10,433,900 | B2 | 10/2019 | Harris et al. |
| 10,441,279 | B2 | 10/2019 | Shelton, IV et al. |
| 10,441,308 | B2 | 10/2019 | Robertson |
| 10,441,310 | B2 | 10/2019 | Olson et al. |
| 10,441,345 | B2 | 10/2019 | Aldridge et al. |
| 10,448,948 | B2 | 10/2019 | Shelton, IV et al. |
| 10,448,950 | B2 | 10/2019 | Shelton, IV et al. |
| 10,448,986 | B2 | 10/2019 | Zikorus et al. |
| 10,456,140 | B2 | 10/2019 | Shelton, IV et al. |
| 10,456,193 | B2 | 10/2019 | Yates et al. |
| 10,463,421 | B2 | 11/2019 | Boudreaux et al. |
| 10,463,887 | B2 | 11/2019 | Witt et al. |
| 10,470,762 | B2 | 11/2019 | Leimbach et al. |
| 10,470,764 | B2 | 11/2019 | Baxter, III et al. |
| 10,478,182 | B2 | 11/2019 | Taylor |
| 10,478,190 | B2 | 11/2019 | Miller et al. |
| 10,485,542 | B2 | 11/2019 | Shelton, IV et al. |
| 10,485,543 | B2 | 11/2019 | Shelton, IV et al. |
| 10,485,607 | B2 | 11/2019 | Strobl et al. |
| D869,655 | S | 12/2019 | Shelton, IV et al. |
| 10,492,785 | B2 | 12/2019 | Overmyer et al. |
| 10,492,849 | B2 | 12/2019 | Juergens et al. |
| 10,499,914 | B2 | 12/2019 | Huang et al. |
| 10,507,033 | B2 | 12/2019 | Dickerson et al. |
| 10,512,795 | B2 | 12/2019 | Voegele et al. |
| 10,517,595 | B2 | 12/2019 | Hunter et al. |
| 10,517,596 | B2 | 12/2019 | Hunter et al. |
| 10,517,627 | B2 | 12/2019 | Timm et al. |
| 10,524,787 | B2 | 1/2020 | Shelton, IV et al. |
| 10,524,789 | B2 | 1/2020 | Swayze et al. |
| 10,524,854 | B2 | 1/2020 | Woodruff et al. |
| 10,524,872 | B2 | 1/2020 | Stewart et al. |
| 10,531,874 | B2 | 1/2020 | Morgan et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,979 | B2 | 1/2020 | Shelton, IV et al. |
| 10,542,982 | B2 | 1/2020 | Beckman et al. |
| 10,542,991 | B2 | 1/2020 | Shelton, IV et al. |
| 10,543,008 | B2 | 1/2020 | Vakharia et al. |
| 10,548,504 | B2 | 2/2020 | Shelton, IV et al. |
| 10,548,655 | B2 | 2/2020 | Scheib et al. |
| 10,555,769 | B2 | 2/2020 | Worrell et al. |
| 10,561,560 | B2 | 2/2020 | Boutoussov et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,632 | B2 | 2/2020 | Miller et al. |
| 10,575,892 | B2 | 3/2020 | Danziger et al. |
| 10,582,928 | B2 | 3/2020 | Hunter et al. |
| 10,588,625 | B2 | 3/2020 | Weaner et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,595,929 | B2 | 3/2020 | Boudreaux et al. |
| 10,595,930 | B2 | 3/2020 | Scheib et al. |
| 10,603,036 | B2 | 3/2020 | Hunter et al. |
| 10,610,224 | B2 | 4/2020 | Shelton, IV et al. |
| 10,610,286 | B2 | 4/2020 | Wiener et al. |
| 10,610,313 | B2 | 4/2020 | Bailey et al. |
| 10,617,412 | B2 | 4/2020 | Shelton, IV et al. |
| 10,617,420 | B2 | 4/2020 | Shelton, IV et al. |
| 10,617,464 | B2 | 4/2020 | Duppuis |
| 10,624,635 | B2 | 4/2020 | Harris et al. |
| 10,624,691 | B2 | 4/2020 | Wiener et al. |
| 10,631,858 | B2 | 4/2020 | Burbank |
| 10,631,859 | B2 | 4/2020 | Shelton, IV et al. |
| 10,632,630 | B2 | 4/2020 | Cao et al. |
| RE47,996 | E | 5/2020 | Turner et al. |
| 10,639,034 | B2 | 5/2020 | Harris et al. |
| 10,639,035 | B2 | 5/2020 | Shelton, IV et al. |
| 10,639,037 | B2 | 5/2020 | Shelton, IV et al. |
| 10,639,092 | B2 | 5/2020 | Corbett et al. |
| 10,639,098 | B2 | 5/2020 | Cosman et al. |
| 10,646,269 | B2 | 5/2020 | Worrell et al. |
| 10,646,292 | B2 | 5/2020 | Solomon et al. |
| 10,653,413 | B2 | 5/2020 | Worthington et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,677,764 | B2 | 6/2020 | Ross et al. |
| 10,682,136 | B2 | 6/2020 | Harris et al. |
| 10,682,138 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,884 | B2 | 6/2020 | Wiener et al. |
| 10,688,321 | B2 | 6/2020 | Wiener et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,119 | B2 | 6/2020 | Smith |
| 10,702,270 | B2 | 7/2020 | Shelton, IV et al. |
| 10,702,329 | B2 | 7/2020 | Strobl et al. |
| 10,709,446 | B2 | 7/2020 | Harris et al. |
| 10,709,469 | B2 | 7/2020 | Shelton, IV et al. |
| 10,709,906 | B2 | 7/2020 | Nield |
| 10,716,615 | B2 | 7/2020 | Shelton, IV et al. |
| 10,722,233 | B2 | 7/2020 | Wellman |
| D893,717 | S | 8/2020 | Messerly et al. |
| 10,729,458 | B2 | 8/2020 | Stoddard et al. |
| 10,729,494 | B2 | 8/2020 | Parihar et al. |
| 10,736,629 | B2 | 8/2020 | Shelton, IV et al. |
| 10,736,685 | B2 | 8/2020 | Wiener et al. |
| 10,751,108 | B2 | 8/2020 | Yates et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,294 | B2 | 9/2020 | Jones |
| 10,765,427 | B2 | 9/2020 | Shelton, IV et al. |
| 10,765,470 | B2 | 9/2020 | Yates et al. |
| 10,772,629 | B2 | 9/2020 | Shelton, IV et al. |
| 10,772,630 | B2 | 9/2020 | Wixey |
| 10,779,821 | B2 | 9/2020 | Harris et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,845 | B2 | 9/2020 | Timm et al. |
| 10,779,849 | B2 | 9/2020 | Shelton, IV et al. |
| 10,779,879 | B2 | 9/2020 | Yates et al. |
| 10,786,253 | B2 | 9/2020 | Shelton, IV et al. |
| 10,786,276 | B2 | 9/2020 | Hirai et al. |
| 10,806,454 | B2 | 10/2020 | Kopp |
| 10,813,638 | B2 | 10/2020 | Shelton, IV et al. |
| 10,820,938 | B2 | 11/2020 | Fischer et al. |
| 10,828,058 | B2 | 11/2020 | Shelton, IV et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |

(56)          References Cited

U.S. PATENT DOCUMENTS

| | | | |
|---|---|---|---|
| 10,835,307 | B2 | 11/2020 | Shelton, IV et al. |
| 10,842,492 | B2 | 11/2020 | Shelton, IV et al. |
| 10,842,523 | B2 | 11/2020 | Shelton, IV et al. |
| 10,842,563 | B2 | 11/2020 | Gilbert et al. |
| D906,355 | S | 12/2020 | Messerly et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,856,896 | B2 | 12/2020 | Eichmann et al. |
| 10,856,929 | B2 | 12/2020 | Yates et al. |
| 10,856,934 | B2 | 12/2020 | Trees et al. |
| 10,874,465 | B2 | 12/2020 | Weir et al. |
| D908,216 | S | 1/2021 | Messerly et al. |
| 10,881,399 | B2 | 1/2021 | Shelton, IV et al. |
| 10,881,401 | B2 | 1/2021 | Baber et al. |
| 10,881,409 | B2 | 1/2021 | Cabrera |
| 10,881,449 | B2 | 1/2021 | Boudreaux et al. |
| 10,888,322 | B2 | 1/2021 | Morgan et al. |
| 10,888,347 | B2 | 1/2021 | Witt et al. |
| 10,893,863 | B2 | 1/2021 | Shelton, IV et al. |
| 10,893,864 | B2 | 1/2021 | Harris et al. |
| 10,893,883 | B2 | 1/2021 | Dannaher |
| 10,898,186 | B2 | 1/2021 | Bakos et al. |
| 10,898,256 | B2 | 1/2021 | Yates et al. |
| 10,912,559 | B2 | 2/2021 | Harris et al. |
| 10,912,580 | B2 | 2/2021 | Green et al. |
| 10,912,603 | B2 | 2/2021 | Boudreaux et al. |
| 10,918,385 | B2 | 2/2021 | Overmyer et al. |
| 10,925,659 | B2 | 2/2021 | Shelton, IV et al. |
| D914,878 | S | 3/2021 | Shelton, IV et al. |
| 10,932,766 | B2 | 3/2021 | Tesar et al. |
| 10,932,847 | B2 | 3/2021 | Yates et al. |
| 10,945,727 | B2 | 3/2021 | Shelton, IV et al. |
| 10,952,788 | B2 | 3/2021 | Asher et al. |
| 10,959,727 | B2 | 3/2021 | Hunter et al. |
| 10,966,741 | B2 | 4/2021 | Illizaliturri-Sanchez et al. |
| 10,966,747 | B2 | 4/2021 | Worrell et al. |
| 10,973,516 | B2 | 4/2021 | Shelton, IV et al. |
| 10,973,517 | B2 | 4/2021 | Wixey |
| 10,973,520 | B2 | 4/2021 | Shelton, IV et al. |
| 10,980,536 | B2 | 4/2021 | Weaner et al. |
| 10,987,123 | B2 | 4/2021 | Weir et al. |
| 10,987,156 | B2 | 4/2021 | Trees et al. |
| 10,993,715 | B2 | 5/2021 | Shelton, IV et al. |
| 10,993,716 | B2 | 5/2021 | Shelton, IV et al. |
| 10,993,763 | B2 | 5/2021 | Batross et al. |
| 11,000,278 | B2 | 5/2021 | Shelton, IV et al. |
| 11,000,279 | B2 | 5/2021 | Shelton, IV et al. |
| 11,020,114 | B2 | 6/2021 | Shelton, IV et al. |
| 11,039,834 | B2 | 6/2021 | Harris et al. |
| 11,045,191 | B2 | 6/2021 | Shelton, IV et al. |
| 11,045,192 | B2 | 6/2021 | Harris et al. |
| 11,058,424 | B2 | 7/2021 | Shelton, IV et al. |
| 11,064,997 | B2 | 7/2021 | Shelton, IV et al. |
| 11,065,048 | B2 | 7/2021 | Messerly et al. |
| 11,083,455 | B2 | 8/2021 | Shelton, IV et al. |
| 11,083,458 | B2 | 8/2021 | Harris et al. |
| 11,090,048 | B2 | 8/2021 | Fanelli et al. |
| 11,090,049 | B2 | 8/2021 | Bakos et al. |
| 11,096,688 | B2 | 8/2021 | Shelton, IV et al. |
| 11,109,866 | B2 | 9/2021 | Shelton, IV et al. |
| 11,129,611 | B2 | 9/2021 | Shelton, IV et al. |
| 11,129,666 | B2 | 9/2021 | Messerly et al. |
| 11,134,942 | B2 | 10/2021 | Harris et al. |
| 11,141,154 | B2 | 10/2021 | Shelton, IV et al. |
| 11,147,551 | B2 | 10/2021 | Shelton, IV |
| 11,147,553 | B2 | 10/2021 | Shelton, IV |
| 11,160,551 | B2 | 11/2021 | Shelton, IV et al. |
| 11,166,716 | B2 | 11/2021 | Shelton, IV et al. |
| 11,172,929 | B2 | 11/2021 | Shelton, IV |
| 11,179,155 | B2 | 11/2021 | Shelton, IV et al. |
| 11,191,539 | B2 | 12/2021 | Overmyer et al. |
| 11,191,540 | B2 | 12/2021 | Aronhalt et al. |
| 11,197,668 | B2 | 12/2021 | Shelton, IV et al. |
| 11,207,065 | B2 | 12/2021 | Harris et al. |
| 11,207,067 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,219,453 | B2 | 1/2022 | Shelton, IV et al. |
| 11,224,426 | B2 | 1/2022 | Shelton, IV et al. |
| 11,224,497 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,241,235 | B2 | 2/2022 | Shelton, IV et al. |
| 11,246,592 | B2 | 2/2022 | Shelton, IV et al. |
| 11,246,625 | B2 | 2/2022 | Kane et al. |
| 11,246,678 | B2 | 2/2022 | Shelton, IV et al. |
| 11,253,256 | B2 | 2/2022 | Harris et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,272,931 | B2 | 3/2022 | Boudreaux et al. |
| 11,278,280 | B2 | 3/2022 | Shelton, IV et al. |
| 11,284,890 | B2 | 3/2022 | Nalagatla et al. |
| 11,291,440 | B2 | 4/2022 | Harris et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,451 | B2 | 4/2022 | Shelton, IV |
| 11,311,342 | B2 | 4/2022 | Parihar et al. |
| D950,728 | S | 5/2022 | Bakos et al. |
| D952,144 | S | 5/2022 | Boudreaux |
| 2001/0025173 | A1 | 9/2001 | Ritchie et al. |
| 2001/0025183 | A1 | 9/2001 | Shahidi |
| 2001/0025184 | A1 | 9/2001 | Messerly |
| 2001/0031950 | A1 | 10/2001 | Ryan |
| 2001/0039419 | A1 | 11/2001 | Francischelli et al. |
| 2002/0002377 | A1 | 1/2002 | Cimino |
| 2002/0002380 | A1 | 1/2002 | Bishop |
| 2002/0019649 | A1 | 2/2002 | Sikora et al. |
| 2002/0022836 | A1 | 2/2002 | Goble et al. |
| 2002/0029036 | A1 | 3/2002 | Goble et al. |
| 2002/0029055 | A1 | 3/2002 | Bonutt |
| 2002/0032452 | A1 | 3/2002 | Tierney et al. |
| 2002/0049551 | A1 | 4/2002 | Friedman et al. |
| 2002/0052617 | A1 | 5/2002 | Anis et al. |
| 2002/0077550 | A1 | 6/2002 | Rabiner et al. |
| 2002/0107517 | A1 | 8/2002 | Witt et al. |
| 2002/0156466 | A1 | 10/2002 | Sakural et al. |
| 2002/0156493 | A1 | 10/2002 | Houser et al. |
| 2002/0165577 | A1 | 11/2002 | Witt et al. |
| 2002/0177862 | A1 | 11/2002 | Aranyi et al. |
| 2003/0009164 | A1 | 1/2003 | Woloszko et al. |
| 2003/0014053 | A1 | 1/2003 | Nguyen et al. |
| 2003/0014087 | A1 | 1/2003 | Fang et al. |
| 2003/0036705 | A1 | 2/2003 | Hare et al. |
| 2003/0040758 | A1 | 2/2003 | Wang et al. |
| 2003/0050572 | A1 | 3/2003 | Brautigam et al. |
| 2003/0055443 | A1 | 3/2003 | Spotnitz |
| 2003/0073981 | A1 | 4/2003 | Whitman et al. |
| 2003/0109778 | A1 | 6/2003 | Rashidi |
| 2003/0109875 | A1 | 6/2003 | Tetzlaff et al. |
| 2003/0114851 | A1 | 6/2003 | Truckal et al. |
| 2003/0130693 | A1 | 7/2003 | Levin et al. |
| 2003/0139741 | A1 | 7/2003 | Goble et al. |
| 2003/0144680 | A1 | 7/2003 | Kellogg et al. |
| 2003/0158548 | A1 | 8/2003 | Phan et al. |
| 2003/0171747 | A1 | 9/2003 | Kanehira et al. |
| 2003/0181898 | A1 | 9/2003 | Bowers |
| 2003/0199794 | A1 | 10/2003 | Sakural et al. |
| 2003/0204199 | A1 | 10/2003 | Novak et al. |
| 2003/0208186 | A1 | 11/2003 | Moreyra |
| 2003/0212332 | A1 | 11/2003 | Fenton et al. |
| 2003/0212363 | A1 | 11/2003 | Shipp |
| 2003/0212392 | A1 | 11/2003 | Fenton et al. |
| 2003/0212422 | A1 | 11/2003 | Fenton et al. |
| 2003/0225332 | A1 | 12/2003 | Okada et al. |
| 2003/0229344 | A1 | 12/2003 | Dycus et al. |
| 2004/0030254 | A1 | 2/2004 | Babaev |
| 2004/0030330 | A1 | 2/2004 | Brassell et al. |
| 2004/0047485 | A1 | 3/2004 | Sherrit et al. |

(56)  References Cited

U.S. PATENT DOCUMENTS

| | | |
|---|---|---|
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033280 A1* | 2/2005 | Francischelli ..... A61B 18/1445 |
| | | 606/41 |
| 2005/0033337 A1 | 2/2005 | Muir et al. |
| 2005/0070800 A1 | 3/2005 | Takahasht |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0119654 A1* | 6/2005 | Swanson ................ A61B 18/18 |
| | | 606/49 |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckal et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0244410 A1* | 10/2007 | Fridman .................. A61B 5/24 |
| | | 600/554 |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |

(56)                References Cited

U.S. PATENT DOCUMENTS

| | | |
|---|---|---|
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whavne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckal et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0112206 A1* | 4/2009 | Dumbauld ......... A61B 18/1445 |
| | | 606/51 |
| 2009/0118751 A1 | 5/2009 | Wiener et al. |
| 2009/0125026 A1 | 5/2009 | Rioux et al. |
| 2009/0131885 A1 | 5/2009 | Akahoshi |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanal et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0282813 A1 | 11/2010 | Milliman |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |

(56)     References Cited

U.S. PATENT DOCUMENTS

| | | |
|---|---|---|
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0234893 A1 | 9/2012 | Schuckmann et al. |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0373003 A1 | 12/2014 | Grez et al. |
| 2015/0014392 A1 | 1/2015 | Williams et al. |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0088122 A1 | 3/2015 | Jensen |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0238260 A1 | 8/2015 | Nau, Jr. |
| 2015/0257780 A1 | 9/2015 | Houser |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0374430 A1 | 12/2015 | Weiler et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051316 A1 | 2/2016 | Boudreaux |
| 2016/0066913 A1 | 3/2016 | Swayze et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0206363 A1 | 7/2016 | Mehta et al. |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0358849 A1 | 12/2016 | Jur et al. |
| 2016/0367281 A1 | 12/2016 | Gee et al. |
| 2017/0000516 A1 | 1/2017 | Stulen et al. |
| 2017/0000541 A1 | 1/2017 | Yates et al. |
| 2017/0000553 A1 | 1/2017 | Wiener et al. |
| 2017/0065331 A1 | 3/2017 | Mayer et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202607 A1 | 7/2017 | Shelton, IV et al. |
| 2017/0224332 A1 | 8/2017 | Hunter et al. |
| 2017/0231628 A1 | 8/2017 | Shelton, IV et al. |
| 2017/0281186 A1 | 10/2017 | Shelton, IV et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348044 A1 | 12/2017 | Wang et al. |
| 2018/0014872 A1 | 1/2018 | Dickerson |
| 2018/0098785 A1 | 4/2018 | Price et al. |
| 2018/0132850 A1 | 5/2018 | Leimbach et al. |
| 2018/0146976 A1 | 5/2018 | Clauda et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0221045 A1 | 8/2018 | Zimmerman et al. |
| 2018/0235691 A1 | 8/2018 | Voegele et al. |

(56) References Cited

U.S. PATENT DOCUMENTS

| | | | |
|---|---|---|---|
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0353245 A1 | 12/2018 | Mccloud et al. |
| 2018/0368843 A1 | 12/2018 | Shelton, IV et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0038279 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0104919 A1 | 4/2019 | Shelton, IV et al. |
| 2019/0105067 A1 | 4/2019 | Boudreaux et al. |
| 2019/0125384 A1 | 5/2019 | Scheib et al. |
| 2019/0125390 A1 | 5/2019 | Shelton, IV et al. |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0201020 A1 | 7/2019 | Shelton, IV et al. |
| 2019/0201023 A1 | 7/2019 | Shelton, IV et al. |
| 2019/0201030 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209201 A1 | 7/2019 | Boudreaux et al. |
| 2019/0223941 A1 | 7/2019 | Kitamura et al. |
| 2019/0262030 A1 | 8/2019 | Faller et al. |
| 2019/0269455 A1 | 9/2019 | Mensch et al. |
| 2019/0274700 A1 | 9/2019 | Robertson et al. |
| 2019/0282288 A1 | 9/2019 | Boudreaux |
| 2019/0282292 A1 | 9/2019 | Wiener et al. |
| 2019/0290265 A1 | 9/2019 | Shelton, IV et al. |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0030021 A1 | 1/2020 | Yates et al. |
| 2020/0054321 A1 | 2/2020 | Harris et al. |
| 2020/0054382 A1 | 2/2020 | Yates et al. |
| 2020/0078076 A1 | 3/2020 | Henderson et al. |
| 2020/0078106 A1 | 3/2020 | Henderson et al. |
| 2020/0078609 A1 | 3/2020 | Messerly et al. |
| 2020/0085465 A1 | 3/2020 | Timm et al. |
| 2020/0100825 A1 | 4/2020 | Henderson et al. |
| 2020/0100830 A1 | 4/2020 | Henderson et al. |
| 2020/0113624 A1 | 4/2020 | Worrell et al. |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0222135 A1 | 7/2020 | Stulen et al. |
| 2020/0229833 A1 | 7/2020 | Vakharia et al. |
| 2020/0229834 A1 | 7/2020 | Olson et al. |
| 2020/0237434 A1 | 7/2020 | Schelb et al. |
| 2020/0261075 A1 | 8/2020 | Boudreaux et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261141 A1 | 8/2020 | Wiener et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0405296 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405312 A1 | 12/2020 | Shelton, IV et al. |
| 2020/0405314 A1 | 12/2020 | Shelton, IV et al. |
| 2020/0405316 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186507 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Flebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |

(56) References Cited

U.S. PATENT DOCUMENTS

| | | |
|---|---|---|
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |

FOREIGN PATENT DOCUMENTS

| | | |
|---|---|---|
| CN | 1233944 A | 11/1999 |
| CN | 1253485 A | 5/2000 |
| CN | 2460047 Y | 11/2001 |
| CN | 1634601 A | 7/2005 |
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 201029899 Y | 3/2008 |
| CN | 101396300 A | 4/2009 |
| CN | 101467917 A | 7/2009 |
| CN | 101474081 A | 7/2009 |
| CN | 101516285 A | 8/2009 |
| CN | 101522112 A | 9/2009 |
| CN | 101674782 A | 3/2010 |
| CN | 101883531 A | 11/2010 |
| CN | 102100582 A | 6/2011 |
| CN | 102149312 A | 8/2011 |
| CN | 102160045 A | 8/2011 |
| CN | 202027624 U | 11/2011 |
| CN | 102792181 A | 11/2012 |
| CN | 102834069 A | 12/2012 |
| CN | 101313865 B | 1/2013 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 204379371 U | 6/2015 |
| CN | 204636479 U | 9/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0443256 A1 | 8/1991 |
| EP | 0456470 A1 | 11/1991 |

| | | |
|---|---|---|
| EP | 0238667 B1 | 2/1993 |
| EP | 0340803 B1 | 8/1993 |
| EP | 0598976 A2 | 6/1994 |
| EP | 0630612 A1 | 12/1994 |
| EP | 0424685 B1 | 5/1995 |
| EP | 0677275 A2 | 10/1995 |
| EP | 0482195 B1 | 1/1996 |
| EP | 0695535 A1 | 2/1996 |
| EP | 0705571 A1 | 4/1996 |
| EP | 0741996 B1 | 11/1996 |
| EP | 0612570 B1 | 6/1997 |
| EP | 0557806 B1 | 5/1998 |
| EP | 0640317 B1 | 9/1999 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 0722696 B1 | 12/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1293172 B1 | 4/2006 |
| EP | 0875209 B1 | 5/2006 |
| EP | 1433425 B1 | 6/2006 |
| EP | 1256323 B1 | 8/2006 |
| EP | 1698289 A2 | 9/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1815950 A1 | 8/2007 |
| EP | 1839599 A1 | 10/2007 |
| EP | 1844720 A1 | 10/2007 |
| EP | 1862133 A1 | 12/2007 |
| EP | 1875875 A1 | 1/2008 |
| EP | 1878399 A1 | 1/2008 |
| EP | 1915953 A1 | 4/2008 |
| EP | 1532933 B1 | 5/2008 |
| EP | 1199045 B1 | 6/2008 |
| EP | 1707143 B1 | 6/2008 |
| EP | 1943957 A2 | 7/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1477104 B1 | 1/2009 |
| EP | 2014218 A2 | 1/2009 |
| EP | 1849424 B1 | 4/2009 |
| EP | 2042112 A2 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 2106758 A1 | 10/2009 |
| EP | 2111813 A1 | 10/2009 |
| EP | 2131760 A1 | 12/2009 |
| EP | 1769766 B1 | 2/2010 |
| EP | 2151201 A1 | 2/2010 |
| EP | 2153791 A1 | 2/2010 |
| EP | 2200145 A1 | 6/2010 |
| EP | 1214913 B1 | 7/2010 |
| EP | 2238938 A1 | 10/2010 |
| EP | 2243439 A1 | 10/2010 |
| EP | 2298154 A2 | 3/2011 |
| EP | 2305144 A1 | 4/2011 |

(56) References Cited

FOREIGN PATENT DOCUMENTS

| | | | |
|---|---|---|---|
| EP | 1510178 B1 | 6/2011 |
| EP | 1946708 B1 | 6/2011 |
| EP | 2335630 A1 | 6/2011 |
| EP | 1502551 B1 | 7/2011 |
| EP | 1728475 B1 | 8/2011 |
| EP | 2353518 A1 | 8/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 1586275 B1 | 5/2013 |
| EP | 1616529 B1 | 9/2013 |
| EP | 1997438 B1 | 11/2013 |
| EP | 2668922 A1 | 12/2013 |
| EP | 2508143 B1 | 2/2014 |
| EP | 2583633 B1 | 10/2014 |
| EP | 2076195 B1 | 12/2015 |
| EP | 2113210 B1 | 3/2016 |
| EP | 2510891 B1 | 6/2016 |
| EP | 2227155 B1 | 7/2016 |
| EP | 2859858 B1 | 12/2016 |
| EP | 3476302 A2 | 5/2019 |
| EP | 3476331 A1 | 5/2019 |
| EP | 3694298 A1 | 8/2020 |
| ES | 2115068 T3 | 6/1998 |
| GB | 1482943 A | 8/1977 |
| GB | 2032221 A | 4/1980 |
| GB | 2317566 A | 4/1998 |
| GB | 2379878 B | 11/2004 |
| GB | 2472216 A | 2/2011 |
| GB | 2447767 B | 8/2011 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04150847 A | 5/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H06217988 A | 8/1994 |
| JP | H06507081 A | 8/1994 |
| JP | H07500514 A | 1/1995 |
| JP | H07508910 A | 10/1995 |
| JP | H07308323 A | 11/1995 |
| JP | H0824266 A | 1/1996 |
| JP | H08229050 A | 9/1996 |
| JP | H08275951 A | 10/1996 |
| JP | H08299351 A | 11/1996 |
| JP | H08336544 A | 12/1996 |
| JP | H08336545 A | 12/1996 |
| JP | H09503146 A | 3/1997 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11501543 A | 2/1999 |
| JP | H11128238 A | 5/1999 |
| JP | H11169381 A | 6/1999 |
| JP | H11192235 A | 7/1999 |
| JP | H11253451 A | 9/1999 |
| JP | H11318918 A | 11/1999 |
| JP | 2000041991 A | 2/2000 |
| JP | 2000070279 A | 3/2000 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2001502216 A | 2/2001 |
| JP | 2001309925 A | 11/2001 |
| JP | 2002059380 A | 2/2002 |
| JP | 2002177295 A | 6/2002 |
| JP | 2002186901 A | 7/2002 |
| JP | 2002204808 A | 7/2002 |
| JP | 2002238919 A | 8/2002 |
| JP | 2002263579 A | 9/2002 |
| JP | 2002301086 A | 10/2002 |
| JP | 2002306504 A | 10/2002 |
| JP | 2002330977 A | 11/2002 |
| JP | 2002542690 A | 12/2002 |
| JP | 2003000612 A | 1/2003 |
| JP | 2003010201 A | 1/2003 |
| JP | 2003510158 A | 3/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003530921 A | 10/2003 |
| JP | 2003310627 A | 11/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005040222 A | 2/2005 |
| JP | 2005066316 A | 3/2005 |
| JP | 2005074088 A | 3/2005 |
| JP | 2005507679 A | 3/2005 |
| JP | 2005534451 A | 11/2005 |
| JP | 2005337119 A | 12/2005 |
| JP | 2006006410 A | 1/2006 |
| JP | 2006068396 A | 3/2006 |
| JP | 2006075376 A | 3/2006 |
| JP | 2006081664 A | 3/2006 |
| JP | 2006114072 A | 4/2006 |
| JP | 2006512149 A | 4/2006 |
| JP | 2006116194 A | 5/2006 |
| JP | 2006158525 A | 6/2006 |
| JP | 2006217716 A | 8/2006 |
| JP | 2006218296 A | 8/2006 |
| JP | 2006288431 A | 10/2006 |
| JP | 2007037568 A | 2/2007 |
| JP | 2007050181 A | 3/2007 |
| JP | 2007524459 A | 8/2007 |
| JP | 2007229454 A | 9/2007 |
| JP | 2007296369 A | 11/2007 |
| JP | 200801876 A | 1/2008 |
| JP | 2008018226 A | 1/2008 |
| JP | 200833644 A | 2/2008 |
| JP | 2008036390 A | 2/2008 |
| JP | 2008508065 A | 3/2008 |
| JP | 2008119250 A | 5/2008 |
| JP | 2008515562 A | 5/2008 |
| JP | 2008521503 A | 6/2008 |
| JP | 2008188160 A | 8/2008 |
| JP | D1339835 S | 8/2008 |
| JP | 2008212679 A | 9/2008 |
| JP | 2008536562 A | 9/2008 |

(56) References Cited

FOREIGN PATENT DOCUMENTS

| | | | |
|---|---|---|---|
| JP | 2008284374 A | 11/2008 |
| JP | 2009511206 A | 3/2009 |
| JP | 2009082711 A | 4/2009 |
| JP | 2009517181 A | 4/2009 |
| JP | 4262923 B2 | 5/2009 |
| JP | 2009523567 A | 6/2009 |
| JP | 2009148557 A | 7/2009 |
| JP | 2009236177 A | 10/2009 |
| JP | 2009254819 A | 11/2009 |
| JP | 2010000336 A | 1/2010 |
| JP | 2010009686 A | 1/2010 |
| JP | 2010514923 A | 5/2010 |
| JP | 2010121865 A | 6/2010 |
| JP | 2010534522 A | 11/2010 |
| JP | 2010540186 A | 12/2010 |
| JP | 2011505198 A | 2/2011 |
| JP | 2012071186 A | 4/2012 |
| JP | 2012075899 A | 4/2012 |
| JP | 2012235658 A | 11/2012 |
| JP | 5208761 B2 | 6/2013 |
| JP | 5714508 B2 | 5/2015 |
| JP | 2015515339 A | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | 9222259 A1 | 12/1992 |
| WO | 9307817 A2 | 4/1993 |
| WO | WO-9308757 A1 | 5/1993 |
| WO | WO-9314708 A1 | 8/1993 |
| WO | 9316646 A1 | 9/1993 |
| WO | 9320877 A1 | 10/1993 |
| WO | 9322973 A1 | 11/1993 |
| WO | 9400059 A1 | 1/1994 |
| WO | 9421183 A1 | 9/1994 |
| WO | 9424949 A1 | 11/1994 |
| WO | 9509572 A1 | 4/1995 |
| WO | 9510978 A1 | 4/1995 |
| WO | 9534259 A1 | 12/1995 |
| WO | 9630885 A1 | 10/1996 |
| WO | 9635382 A1 | 11/1996 |
| WO | WO-9639086 A1 | 12/1996 |
| WO | 9710764 A1 | 3/1997 |
| WO | WO-9800069 A1 | 1/1998 |
| WO | 9816156 A1 | 4/1998 |
| WO | 9826739 A1 | 6/1998 |
| WO | 9835621 A1 | 8/1998 |
| WO | 9837815 A1 | 9/1998 |
| WO | 9840020 A1 | 9/1998 |
| WO | WO-9840015 A2 | 9/1998 |
| WO | 9847436 A1 | 10/1998 |
| WO | 9857588 A1 | 12/1998 |
| WO | WO-9920213 A1 | 4/1999 |
| WO | WO-9923960 A1 | 5/1999 |
| WO | 9940857 A1 | 8/1999 |
| WO | 9940861 A1 | 8/1999 |
| WO | 9952489 A1 | 10/1999 |
| WO | 0024331 A1 | 5/2000 |
| WO | 0025691 A1 | 5/2000 |
| WO | WO-0024330 A1 | 5/2000 |
| WO | WO-0064358 A2 | 11/2000 |
| WO | 0074585 A2 | 12/2000 |
| WO | 0124713 A1 | 4/2001 |
| WO | WO-0128444 A1 | 4/2001 |
| WO | 0154590 A1 | 8/2001 |
| WO | WO-0167970 A1 | 9/2001 |
| WO | WO-0172251 A1 | 10/2001 |
| WO | WO-0195810 A2 | 12/2001 |
| WO | 0224080 A2 | 3/2002 |
| WO | 0238057 A1 | 5/2002 |
| WO | 02062241 A1 | 8/2002 |
| WO | 02080797 A1 | 10/2002 |
| WO | 03001986 A2 | 1/2003 |
| WO | 03013374 A1 | 2/2003 |
| WO | 03020339 A2 | 3/2003 |
| WO | 03028541 A2 | 4/2003 |
| WO | 03030708 A2 | 4/2003 |
| WO | 03068046 A2 | 8/2003 |
| WO | 03082133 A1 | 10/2003 |
| WO | WO-03095028 A1 | 11/2003 |
| WO | 2004011037 A2 | 2/2004 |
| WO | 2004012615 A1 | 2/2004 |
| WO | 2004026104 A2 | 4/2004 |
| WO | 2004032754 A2 | 4/2004 |
| WO | 2004032762 A1 | 4/2004 |
| WO | 2004032763 A2 | 4/2004 |
| WO | WO-2004037095 A2 | 5/2004 |
| WO | 2004060141 A2 | 7/2004 |
| WO | WO-2004078051 A2 | 9/2004 |
| WO | 2004098426 A1 | 11/2004 |
| WO | 2004112618 A2 | 12/2004 |
| WO | 2005052959 A2 | 6/2005 |
| WO | 2005117735 A1 | 12/2005 |
| WO | 2005122917 A1 | 12/2005 |
| WO | 2006012797 A2 | 2/2006 |
| WO | 2006021269 A1 | 3/2006 |
| WO | 2006036706 A1 | 4/2006 |
| WO | 2006042210 A2 | 4/2006 |
| WO | 2006055166 A2 | 5/2006 |
| WO | 2006058223 A2 | 6/2006 |
| WO | 2006063199 A2 | 6/2006 |
| WO | 2006083988 A1 | 8/2006 |
| WO | WO-2006091494 A1 | 8/2006 |
| WO | 2006101661 A2 | 9/2006 |
| WO | 2006119139 A2 | 11/2006 |
| WO | 2006119376 A2 | 11/2006 |
| WO | 2006129465 A1 | 12/2006 |
| WO | 2007008703 A2 | 1/2007 |
| WO | WO-2007008710 A1 | 1/2007 |
| WO | 2007038538 A1 | 4/2007 |
| WO | 2007040818 A1 | 4/2007 |
| WO | 2007047380 A2 | 4/2007 |
| WO | 2007047531 A2 | 4/2007 |
| WO | 2007056590 A1 | 5/2007 |
| WO | 2007087272 A2 | 8/2007 |
| WO | 2007089724 A2 | 8/2007 |
| WO | 2007143665 A2 | 12/2007 |
| WO | 2008016886 A2 | 2/2008 |
| WO | 2008020964 A2 | 2/2008 |
| WO | 2008042021 A1 | 4/2008 |
| WO | 2008045348 A2 | 4/2008 |
| WO | 2008049084 A2 | 4/2008 |
| WO | 2008051764 A2 | 5/2008 |
| WO | 2008089174 A2 | 7/2008 |
| WO | 2008099529 A1 | 8/2008 |
| WO | 2008101356 A1 | 8/2008 |
| WO | WO-2008118709 A1 | 10/2008 |
| WO | WO-2008130793 A1 | 10/2008 |
| WO | 2009010565 A1 | 1/2009 |
| WO | 2009018067 A1 | 2/2009 |
| WO | 2009018406 A2 | 2/2009 |
| WO | 2009022614 A2 | 2/2009 |
| WO | 2009027065 A1 | 3/2009 |
| WO | 2009036818 A1 | 3/2009 |
| WO | 2009039179 A1 | 3/2009 |
| WO | 2009046234 A2 | 4/2009 |
| WO | 2009059741 A1 | 5/2009 |
| WO | 2009073402 A2 | 6/2009 |
| WO | 2009082477 A2 | 7/2009 |
| WO | 2009088550 A2 | 7/2009 |
| WO | 2009120992 A2 | 10/2009 |
| WO | 2009141616 A1 | 11/2009 |
| WO | 2009149234 A2 | 12/2009 |
| WO | 2010017149 A1 | 2/2010 |
| WO | 2010017266 A1 | 2/2010 |
| WO | WO-2010027109 A1 | 3/2010 |
| WO | 2010068783 A1 | 6/2010 |
| WO | WO-2010104755 A1 | 9/2010 |
| WO | WO-2011008672 A2 | 1/2011 |

(56) References Cited

FOREIGN PATENT DOCUMENTS

| WO | 2011044338 A2 | 4/2011 |
| WO | WO-2011044343 A2 | 4/2011 |
| WO | WO-2011052939 A2 | 5/2011 |
| WO | WO-2011060031 A1 | 5/2011 |
| WO | 2011084768 A1 | 7/2011 |
| WO | 2011089717 A1 | 7/2011 |
| WO | 2011100321 A2 | 8/2011 |
| WO | 2011144911 A1 | 11/2011 |
| WO | 2012044597 A1 | 4/2012 |
| WO | WO-2012044606 A2 | 4/2012 |
| WO | 2012061638 A1 | 5/2012 |
| WO | WO-2012061722 A2 | 5/2012 |
| WO | WO-2012088535 A1 | 6/2012 |
| WO | 2012128362 A1 | 9/2012 |
| WO | 2012135705 A1 | 10/2012 |
| WO | 2012135721 A1 | 10/2012 |
| WO | WO-2012150567 A1 | 11/2012 |
| WO | 2012166510 A1 | 12/2012 |
| WO | 2013018934 A1 | 2/2013 |
| WO | 2013034629 A1 | 3/2013 |
| WO | 2013062978 A1 | 5/2013 |
| WO | 2013102602 A2 | 7/2013 |
| WO | 2013154157 A2 | 10/2013 |
| WO | 2014092108 A1 | 6/2014 |
| WO | 2014196641 A1 | 12/2014 |
| WO | 2015197395 A1 | 12/2015 |
| WO | 2016009921 A8 | 1/2016 |
| WO | WO-2016130844 A1 | 8/2016 |
| WO | WO-2019130090 A1 | 7/2019 |
| WO | WO-2019130113 A1 | 7/2019 |

OTHER PUBLICATIONS

"ATM-MPLS Network Interworking Version 2.0, af-aic-0178.001" ATM Standard, The ATM Forum Technical Committee, published Aug. 2003.
Missinne, et al. "Stretchable Optical Waveguides," vol. 22, No. 4, Feb. 18, 2014, pp. 4168-4179 (12 pages).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Hörmann et al., "Reversible and irreversible denaturation of collagen fibers." Biochemistry, 10, pp. 932-937 (1971).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL:http//wonder.cdc.gov/wonder/prevguid/p0000191/p0000191.asp (15 pages).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nim.nih.gov/pmc/articles/PMC2597841/.
Covidien Brochure, The LigaSure Precise™ Instrument, dated Mar. 2011 (2 pages).
AST Products, Inc., "Principles of Video Contact Angle Analysis," 20 pages, (2006).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Heat-induced changes in the mechanics of a collagenous tissue: pseudoelastic behavior at 37° C," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Moraleda et al., A Temperature Sensor Based on a Polymer Optical Fiber Macro-Bend, Sensors 2013, 13, 13076-13089, doi: 10.3390/s131013076, ISSN 1424-8220.
Leonard I. Malis, M.D., "The Value of Irrigation During Bipolar Coagulation," 1989.
http:/www.ethicon.com/gb-en/healthcare-professionals/products/energy-devices/capital//ge . . . .
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al, "Thermal Imaging in Surgery," p. 19-3, in Medical Infrared Imaging, N. A. Diakides and J. D. Bronzino, Eds. (2008).
http://www.dotmed.com/listing/electrosurical-unit/ethicon/ultracision-g110-/1466724.
http://www.4-traders.com/JOHNSON-JOHNSON-4832/news/Johnson-Johnson-Ethicon-E . . . .
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands In a Litz-Wire Transformer Winding," IEEE Transactions on Power Electronics, vol. 14, No. 2, Mar. 1999, pp. 283-291.

(56)            References Cited

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Henriques. F.C., "Studies in thermal injury V. The predictability and the significance of thermally induced rate processes leading to irreversible epidermal injury." Archives of Pathology, 434, pp. 489-502 (1947).

Wall et al., "Thermal modification of collagen," J Shoulder Elbow Surg, No. 8, pp. 339-344 (Jul./Aug. 1999).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Douglas, S.C. "Introduction to Adaptive Filter". Digital Signal Processing Handbook. Ed. Vijay K. Madisetti and Douglas B. Williams. Boca Raton: CRC Press LLC, 1999.

Kurt Gleck & Reiner Gleck, *Engineering Formulas* § Z.7 (7th ed. 1997).

Glaser and Subak-Sharpe,Integrated Circuit Engineering, Addison-Wesley Publishing, Reading, MA (1979). (book—not attached).

Covidien 501 (k) Summary Sonicision, dated Feb. 24, 2011 (7 pages).

http://www.megadyne.com/es_generator.php.

LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

http://www.apicalinstr.com/generators.htm.

http://www.medicalexpo.com/medical-manufacturer/electrosurgical-generator-6951.html.

http://www.valleylab.com/product/es/generators/index.html.

PCT International Search Report and Written Opinion completed Jun. 30, 2017 in Application No. PCT/US2017/030029 , 10 pgs.

IEC 60601-2-10 Medical electrical equipment—Part 2-10: Particular requirements for the basic safety and essential performance of nerve and muscle stimulators, 6 pgs.

* cited by examiner

MEDICAL DEVICE WITH A BILATERAL JAW CONFIGURATION FOR NERVE STIMULATION

This application is a continuation application claiming priority under 35 U.S.C. § 120 to U.S. patent application Ser. No. 16/574,843, entitled "MEDICAL DEVICE WITH A BILATERAL JAW CONFIGURATION FOR NERVE STIMULATION," now U.S. Pat. No. 11,864,820, which was filed on Sep. 18, 2019 and which claims priority under 35 U.S.C. § 120 to U.S. patent application Ser. No. 15/493, 122, entitled "MEDICAL DEVICE WITH A BILATERAL JAW CONFIGURATION FOR NERVE STIMULATION," now U.S. Pat. No. 10,456,193, which was filed on Apr. 20, 2017 and which claims the benefit under 35 U.S.C. § 119(e) of U.S. Provisional Patent Application Ser. No. 62/331,123, entitled "MEDICAL DEVICE WITH A BILATERAL JAW CONFIGURATION FOR NERVE STIMULATION," which was filed on May 3, 2016, filed May 3, 2016, the entire disclosures of each of which are hereby incorporated by reference herein.

TECHNICAL FIELD

The present disclosure is related generally to medical devices with various mechanisms for grasping, cutting, and sealing tissue. In particular, the present disclosure is related to medical devices with grasping instruments that perform nerve stimulation using non-therapeutic energy in one or more probes in the same device.

BACKGROUND

During surgery, energy used to cut and seal tissue, such as ultrasonic vibrations or electrosurgical energy, may be damaging to certain body tissue that is not intended to be operated on though it be present in a surgical site. For example, nerves may be damaged that come into contact with energy applied at surgical and therapeutic levels. On the other hand, low levels of energy applied onto or close to nerves (e.g., ~2 mm) may cause a visible vibration of the associated muscles to alert a surgeon to their presence. This visible indication may provide the surgeon enough information to safely perform the surgery while avoiding delicate nerve endings. Traditionally, surgeons may therefore utilize multiple devices to perform the surgery, such as one device to detect nerves by applying lower voltage to nerve stimulation probes, and another device to grasp, seal, and/or cut tissue by applying ultrasonic or higher voltage therapeutic energy. It may be desirable to utilize a surgical tool that applies therapeutic energy, e.g., ultrasonic or higher voltage electrosurgical energy, and also includes nerve sensing capabilities, such as carefully positioned lower voltage nerve stimulation probes, in a single device to allow for safer and more efficient surgical procedures.

While several devices have been made and used, it is believed that no one prior to the inventors has made or used the device described in the appended claims.

BRIEF SUMMARY

In some aspects, a surgical instrument is provided.

In one example, a surgical instrument is presented comprising: a first jaw handle and a second jaw handle pivotally coupled about a joint; the first jaw handle comprising a first jaw at a distal end of the first jaw handle; the second jaw handle comprising a second jaw at a distal end of the second jaw handle; the first and second jaws configured to grasp tissue therebetween when the first and second jaw handles are pivotally rotated about the joint into a closed position; at least one of the first and second jaws configured to deliver therapeutic energy at a higher energy level for sealing or cutting tissue at a surgical site; and at least one of the first and second jaws configured to deliver nontherapeutic energy at a lower energy level for providing electrical stimulation to nerve tissue at the surgical site.

In another example of the surgical instrument in example 1, the therapeutic energy comprises ultrasonic energy.

In another example of the surgical instrument in example 1, the therapeutic energy comprises high frequency electrosurgical energy.

In another example of the surgical instrument in example 1, both the first and second jaws are configured to deliver the nontherapeutic energy to the tissue at the surgical site, and wherein the nontherapeutic energy delivered at both the first and second jaws are at the same electrical potential.

In another example of the surgical instrument in example 1, at least one of the first and second jaws comprises an insulating material on an inside portion of said jaw such that the first jaw contacts the second jaw in the closed position by way of touching the insulating material.

In another example, a surgical instrument is presented comprising: a handle assembly; and an end effector communicatively coupled to the handle assembly and comprising a first and second jaw, the handle assembly configured to manipulate the first and second jaws to define an open position and a closed position; and the end effector configured to: deliver therapeutic energy at a higher energy level for sealing or cutting tissue at a surgical site; and deliver nontherapeutic energy at a lower energy level for providing electrical stimulation to nerve tissue at the surgical site.

In another example of the surgical instrument in example 6, the end effector further comprises an electrical stimulation probe configured to deliver the nontherapeutic energy to stimulate the nerve tissue at the surgical site.

In another example of the surgical instrument in example 7, the electrical stimulation probe is retractable and is further configured to retract in a proximal direction toward the handle assembly, and to protract in a distal direction away from the handle assembly.

In another example of the surgical instrument in example 7, the end effector further comprises a return probe, wherein the electrical stimulation probe and the return probe complete a circuit when both the return probe and the electrical stimulation probe contact tissue at the surgical site, and wherein the return probe acts as an electrical return for the nontherapeutic energy.

In another example of the surgical instrument in example 7, the electrical stimulation probe is configured to contour substantially near a first side of the end effector, the first side of the end effector including a first portion of a distal tip of the end effector defined by the first and second jaws.

In another example of the surgical instrument in example 10, the end effector further comprises a return probe configured to contour substantially near a second side of the end effector opposite to the first side, the second side of the end effector including a second portion of the distal tip of the end effector defined by the first and second jaws, wherein the electrical stimulation probe and the return probe complete a circuit when both the return probe and the electrical stimulation probe contact tissue at the surgical site.

In another example of the surgical instrument in example 6, the end effector further comprises a first electrical protrusion probe coupled to a distal end of the first or second jaw and configured to deliver the nontherapeutic energy to stimulate the nerve tissue at the surgical site.

In another example of the surgical instrument in example 12, wherein the end effector further comprises a second electrical protrusion return probe coupled to the distal end of the first or second jaw and configured to complete a circuit with the first electrical protrusion when both the first and second probes contact tissue at the surgical site.

In another example of the surgical instrument in example 6, the surgical instrument further comprises a shaft coupled to a distal end of the handle assembly and a proximal end of the end effector, the shaft configured to electrically couple the end effector to the handle assembly.

In another example, a surgical system is presented comprising: a handle assembly; a power generator electrically coupled to the handle assembly; and an end effector communicatively coupled to the handle assembly and electrically coupled to the power generator and comprising a first and second jaw, the handle assembly configured to manipulate the first and second jaws to define an open position and a closed position; the end effector configured to: selectively deliver therapeutic energy at a higher energy level for sealing or cutting tissue at a surgical site; and selectively deliver nontherapeutic energy at a lower energy level for providing electrical stimulation to nerve tissue at the surgical site; the power generator configured to: generate therapeutic energy at the higher energy level to be transmitted to the end effector; and generate nontherapeutic energy at the lower energy level to be transmitted to the end effector.

In another example of the surgical system in example 15, the end effector further comprises an electrical stimulation probe configured to deliver the nontherapeutic energy to stimulate the nerve tissue at the surgical site.

In another example of the surgical system in example 16, the electrical stimulation probe is retractable and is further configured to retract in a proximal direction toward the handle assembly, and to protract in a distal direction away from the handle assembly.

In another example of the surgical system in example 16, the end effector further comprises a return probe, wherein the electrical stimulation probe and the return probe complete a circuit when both the return probe and the electrical stimulation probe contact tissue at the surgical site.

In another example of the surgical system in example 16, the electrical stimulation probe is configured to contour substantially near a first side of the end effector, the first side of the end effector including a first portion of a distal tip of the end effector defined by the first and second jaws.

In another example of the surgical system in example 15, the end effector further comprises a return probe configured to contour substantially near a second side of the end effector opposite to the first side, the second side of the end effector including a second portion of the distal tip of the end effector defined by the first and second jaws, wherein the electrical stimulation probe and the return probe complete a circuit when both the return probe and the electrical stimulation probe contact tissue at the surgical site.

In another example of the surgical system in example 18, the therapeutic energy is monopolar and the return probe further acts as an electrical return for the therapeutic energy.

The foregoing summary is illustrative only and is not intended to be in any way limiting. In addition to the illustrative aspects and features described above, further aspects and features will become apparent by reference to the drawings and the following detailed description.

BRIEF DESCRIPTION OF THE DRAWINGS

The novel features of the aspects described herein are set forth with particularity in the appended claims. These aspects, however, both as to organization and methods of operation may be better understood by reference to the following description, taken in conjunction with the accompanying drawings as follows.

DETAILED DESCRIPTION

Figure 1:
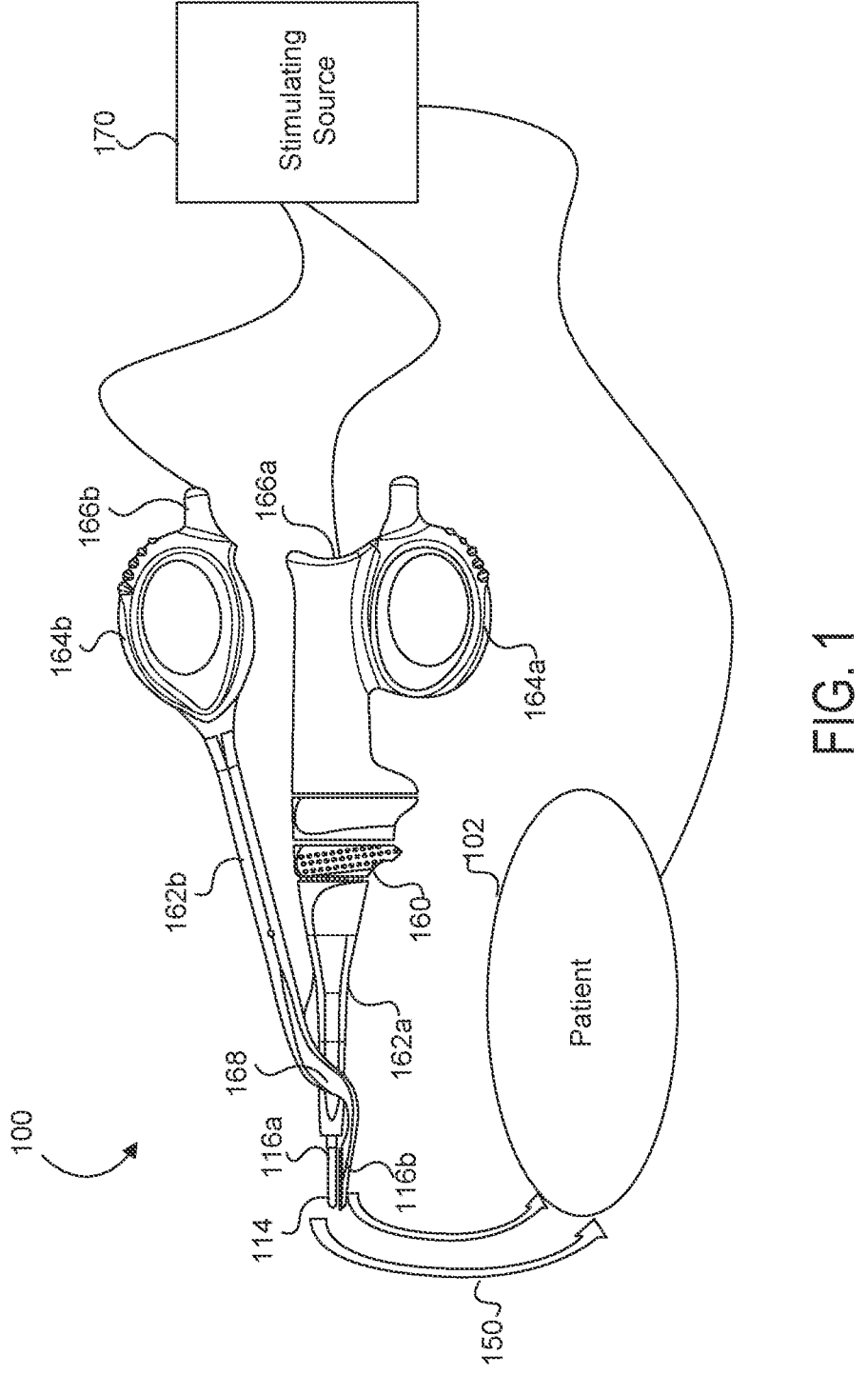
FIG. 1 illustrates a medical device configurable with both nerve stimulation and therapeutic functions, according to various aspects.

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

The following description of certain examples of the technology should not be used to limit its scope. Other examples, features, aspects, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, aspects, examples, etc., described herein may be combined with any one or more of the other teachings, expressions, aspects, examples, etc., that are described herein. The following-described teachings, expressions, aspects, examples, etc., should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, top, bottom, and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component further from the user operating the surgical instrument.

Aspects of the present disclosure are presented for a single surgical instrument configured to grasp, seal, and/or cut tissue through application of therapeutic energy, e.g., ultrasonic and/or higher voltage electrosurgical energy, and also detect nerves through application of non-therapeutic electrical energy. Conventionally, at least two medical devices may be used to perform the combination of these actions. However, visibility may be reduced by having multiple devices crowding the surgical site, making it possibly less safe than if a single device could perform all of the aforementioned functions. Furthermore, a surgeon's precision may be compromised if multiple instruments are alternated in and out of the surgical site to perform different functions repeatedly.

Various features described herein may be incorporated in electrosurgical devices for applying electrical energy to tissue for therapeutic purposes in order to treat and/or destroy the tissue are also finding increasingly widespread applications in surgical procedures. An electrosurgical device typically includes a hand piece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad or dispersive electrode that is attached to or adjacent the patient at a location remote to the surgical site and electrically coupled to the patient capacitively or directly by way of a conductive adhesive) separately located on a patient's body. Heat generated by the current flowing through the tissue may form hemostatic seals within the tissue and/or between tissues and thus may be particularly useful for sealing blood vessels, for example. The end effector of an electrosurgical device may also include a cutting member that is movable relative to the tissue and the electrodes to transect the tissue.

In some aspects, a medical device includes two jaws at an end effector, used to apply therapeutic energy and to perform grasping, sealing, and/or cutting procedures. The end effector may be formed at the distal end of a shaft, the proximal end of the shaft communicatively coupled to a handle assembly. In other cases, the end effector may be formed at the end of a pair of clamp arms in a scissor-like configuration. One or both of the jaws may be configured to supply therapeutic energy, such as in the form of ultrasonic vibrations or higher voltage electrosurgical energy. In some aspects, one of the jaws may be configured to cut tissue through application of a blade. In addition, one or both of the two jaws may be configured to apply nontherapeutic energy for nerve stimulation probing, such as applying lower amplitude electrical energy. In some aspects, the application of therapeutic energy may be disabled while the nontherapeutic nerve stimulation energy is applied, and vice versa. In some aspects, the nontherapeutic nerve stimulation energy may be applied to the use of one or more probes positioned near one or both of the jaws.

Electrical energy applied by an electrosurgical device can be transmitted to the instrument by a generator in communication with the handle assembly. The electrical energy may be in the form of radio frequency ("RF") energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

Referring to FIG. 1, a medical device 100 is illustrated, configurable with both nerve stimulation and therapeutic functions, according to various aspects. The medical device 100 comprises two jaws 116a and 116b at the distal end to define an end effector 114, both jaws separately connected to jaw arms 162a and 162b, respectively. Jaw handles 164a and 164b are coupled to the jaw arms 162a and 162, respectively, at the proximal ends. The jaws 116a and 116b may be pivotally connected at a joint 168, thereby allowing the jaws to clamp and/or grasp tissue between them. In some aspects, one or both of the jaws 116a and 116b may be configured to deliver therapeutic energy to the contact tissue through various means, such as ultrasonic energy, high frequency electrosurgical energy, resistive heating elements, microwaves, and so forth. In some aspects, an activation switch, roller, or button 160 may be included in one of the arms to adjust the degree of therapeutic energy.

In addition, the medical device 100 may be configured to deliver nontherapeutic, nerve stimulation probing energy at one or both of the jaws 116a and 160b. This energy may be formed at a low frequency or voltage so as to not damage any nerves or other tissues when the jaws 116a and 116b come into contact with tissue in this mode. In some aspects, both of the jaws may be configured to deliver the nontherapeutic probing energy to create a bilateral nerve stimulation configuration. A stimulating source 170 may be electrically coupled to the medical device 100, such as through the energy ports 166a and 166b, to supply the probing energy through the two jaw handles 164a and 164b. Both of the jaws may be receiving energy at the same electrical potential. The energy may then be applied to the patient 102 through the jaws 116a and 116b, as indicated by the arrows 150. The electrical stimulation path may be completed through use of, for example a subdermal needle probe, a patient grounding clip wire, or patient grounding pad. Thus, when in this configuration, the medical device 100 may be configured to detect when the jaws 116a and/or 116b approach any nerves at a surgical site. For example, application of this energy touching or nearly touching (e.g., ~2 mm) the nerves may result in a visible vibration of the nerve, to indicate to the surgeon the presence of the nerve.

In some aspects, locating the nerves by this type of stimulation may be achieved through any of three desired usage modes. In one case, nerves may be queried through probing by the tips of the jaws 116a and 116b. That is, nerves or other non-muscle tissue may twitch or vibrate if the tips of the jaws 116a and/or 116b are on or near (e.g., ~1-5 mm) them. In testing with about 0.5 mA stimulation output, nerves are typically stimulated when the conducting member (tips of the jaws 116a and/or 116b) is on or touching the nerve or touching tissue that is immediately adjacent (less than about 1 mm) to the nerve. Likewise, with a 2 mA stimulation output, nerves are typically stimulated when the conducting member touches adjacent tissue that is at about 2 to 5 mm from the nerve. A second case includes clamping of tissue to detect the nerves. At least one inside clapping surface of one of the jaws 116a or 116b is configured to apply the nerve stimulation energy. A third case includes detection through spread dissection. Spreading tissue by widening the jaws may detect nerves with at least one of the outside surfaces configured to be active to apply the non-therapeutic nerve stimulation energy. In other configurations, more than one of these usage modes may be implemented in the medical device 100.

In some aspects, the jaws 116a and 116b may be electrically isolated even when the jaws are in a closed position or are grasping tissue. Insulating pins may be placed on the inside of at least one of the jaws 116a or 116b, such that the jaws touch only at the insulating pins. In other cases, insulating bands or other non conductive materials may be positioned around one or both of the jaws 116a or 116b such that the jaws touch only at the insulating bands or other non conductive materials. In this way, sufficient physical space may be allocated to allow for ultrasonic vibratory isolation, or in other cases for electrical isolation as may be utilized with bipolar electrosurgery jaws.

Figure 2:
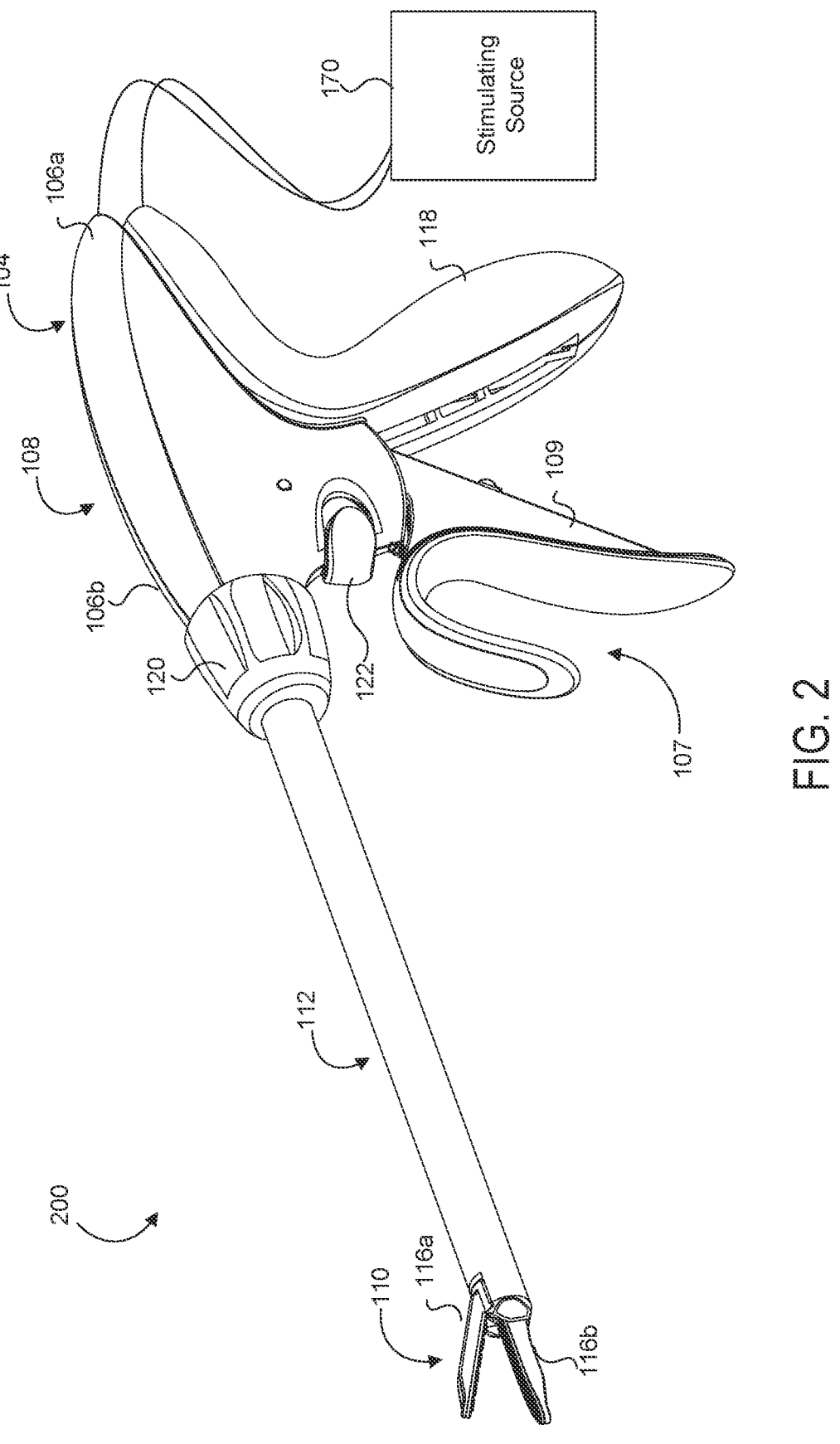
FIG. 2 illustrates an alternative design of a surgical instrument configured to deliver therapeutic and nontherapeutic energy to a surgical site, according to some aspects.

FIG. 2 illustrates an alternative design of a surgical instrument 200 configured to deliver therapeutic and non-therapeutic energy to a surgical site, according to some aspects. The instrument 200 may include a trigger assembly 107 and a closure system arrangement for closing the jaws 116a and 116b at the end effector 110 comprising a spring driven cam closure mechanism, according to some aspects. The spring driven cam closure system is configured to close the set of opposing jaws 116a, 116b, and in some cases fire a cutting element in the end effector 110. The trigger assembly 107 is configured to clamp and fire an end effector 110 coupled to the shaft assembly 112 of the surgical instrument 200. The surgical instrument 200 also includes a handle assembly 104, a shaft assembly 112, and the end effector 110. The shaft assembly 112 comprises a proximal end and a distal end. The proximal end of the shaft assembly 112 is coupled to the distal end of the handle assembly 104. The end effector 110 is coupled to the distal end of the shaft assembly 112. The handle assembly 104 comprises a pistol grip 118. The handle assembly 104 comprises a left handle housing shroud 106a and a right handle housing shroud 106b. The trigger assembly 107 comprises a trigger 109 actuatable towards the pistol grip 118. A rotatable shaft knob 120 is configured to rotate the shaft assembly 112 with respect to the handle assembly 104. The handle assembly 104 further comprises an energy button 122 configured to provide therapeutic electrosurgical energy to one or more electrodes in the end effector 110. The shaft assembly 112 comprises a closure/jaw actuator, a firing/cutting member actuator, and an outer sheath. In some aspects, the outer sheath comprises the closure actuator. The outer sheath comprises one or more contact electrodes on a distal end configured to interface with the end effector 110. The one or more contact electrodes are operatively coupled to the energy button 122, the tissue sealer mode selection assembly 108, and the stimulating source 170.

The energy source may be suitable for therapeutic tissue treatment, tissue cauterization/sealing, as well as sub-therapeutic treatment and measurement. The energy button 122 controls the delivery of energy to the electrodes. The device 200 also is configured to switch to applying non-therapeutic energy at the end effector 110, in some cases through a toggle switch or button, such as by pressing energy button 122 a second time to switch to nerve stimulation mode. In other cases, a separate button or switch activation, such as through rotating the knob 120 into a certain orientation, or pressing another button, not shown, may allow for the activation of the nerve stimulation energy. The stimulating source 170 may be configured to generate energy for one or both modes. Additional example details for the energy generation waveforms will be described in more detail, below.

It will be appreciated that the user may select a treatment or diagnostic output or the system may select a treatment or diagnostic output as appropriate to the situation.

As used throughout this disclosure, a button refers to a switch mechanism for controlling some aspect of a machine or a process. The buttons may be made out of a hard material such as usually plastic or metal. The surface may be formed or shaped to accommodate the human finger or hand, so as to be easily depressed or pushed. Buttons can be most often biased switches, even though many un-biased buttons (due to their physical nature) require a spring to return to their un-pushed state. Terms for the "pushing" of the button, may include press, depress, mash, and punch.

Figure 11:
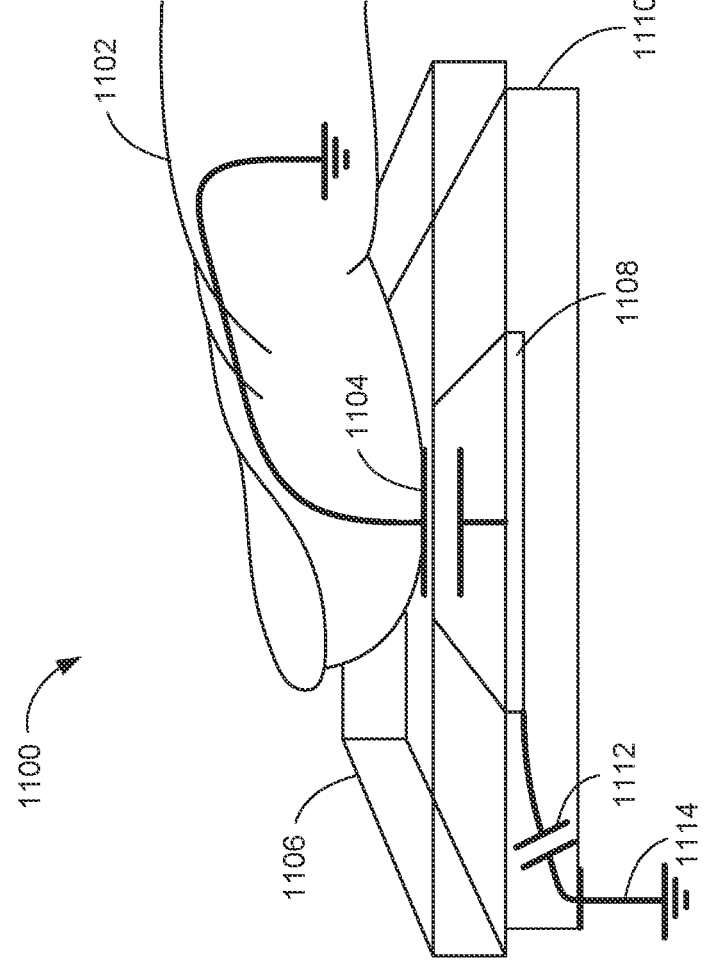
FIG. 11 illustrates a button based on a capacitive switch, according to some aspects.

FIG. 11 illustrates a button based on a capacitive switch, according to some aspects of the present disclosure. In other aspects, the button could be based on optical interrupter technology. Returning to FIG. 11, a capacitive touch switch system 1100 is shown. The capacitive touch switch 1100 comprises an electrically insulative cover plate 1106 located above a printed circuit board substrate 1110. An electrically conductive pad 1108, usually formed of copper or other electrically conductive metal. The capacitive touch switch 1100 is formed when a finger 1102 touches the cover plate 1106 and a finger capacitance 1104 is developed between the finger 1102 and the electrically conductive pad 1108 located below the cover plate 1106. The finger capacitance 1104 is coupled to ground through the person's body. When the finger 1102 is in contact with the cover plate 1106, the finger capacitance 1104 is in parallel with the pad capacitance 1112 which is coupled to a ground 1114 located elsewhere in the system. The capacitive touch switch system 1100 is one example of how buttons employed in the example surgical devices may be implemented.

Referring back to FIG. 2, in some aspects, the end effector 110 is coupled to the distal end of the shaft assembly 112. The end effector 110 comprises a first jaw member 116a and a second jaw member 116b. The first jaw member 116a is pivotally coupled to the second jaw member 116b. The first jaw member 116a is pivotally moveable with respect to the second jaw member 116b to grasp tissue therebetween. In some aspects, the second jaw member 116b is fixed. In other aspects, the first jaw member 116a and the second jaw member 116b are pivotally movable. The end effector 110 comprises at least one electrode. The electrode is configured to deliver electrosurgical energy. Energy delivered by the electrode may comprise, for example, radiofrequency (RF) energy, sub-therapeutic RF energy, ultrasonic energy, and/or other suitable forms of energy. In some aspects, a cutting member (not shown) is receivable within a longitudinal slot defined by the first jaw member 116a and/or the second jaw member 116b. The cutting member is configured to cut tissue grasped between the first jaw member 116a and the second jaw member 116b. In some aspects, the cutting member comprises an electrode for delivering energy, such as, for example, RF and/or ultrasonic energy.

Figure 3:
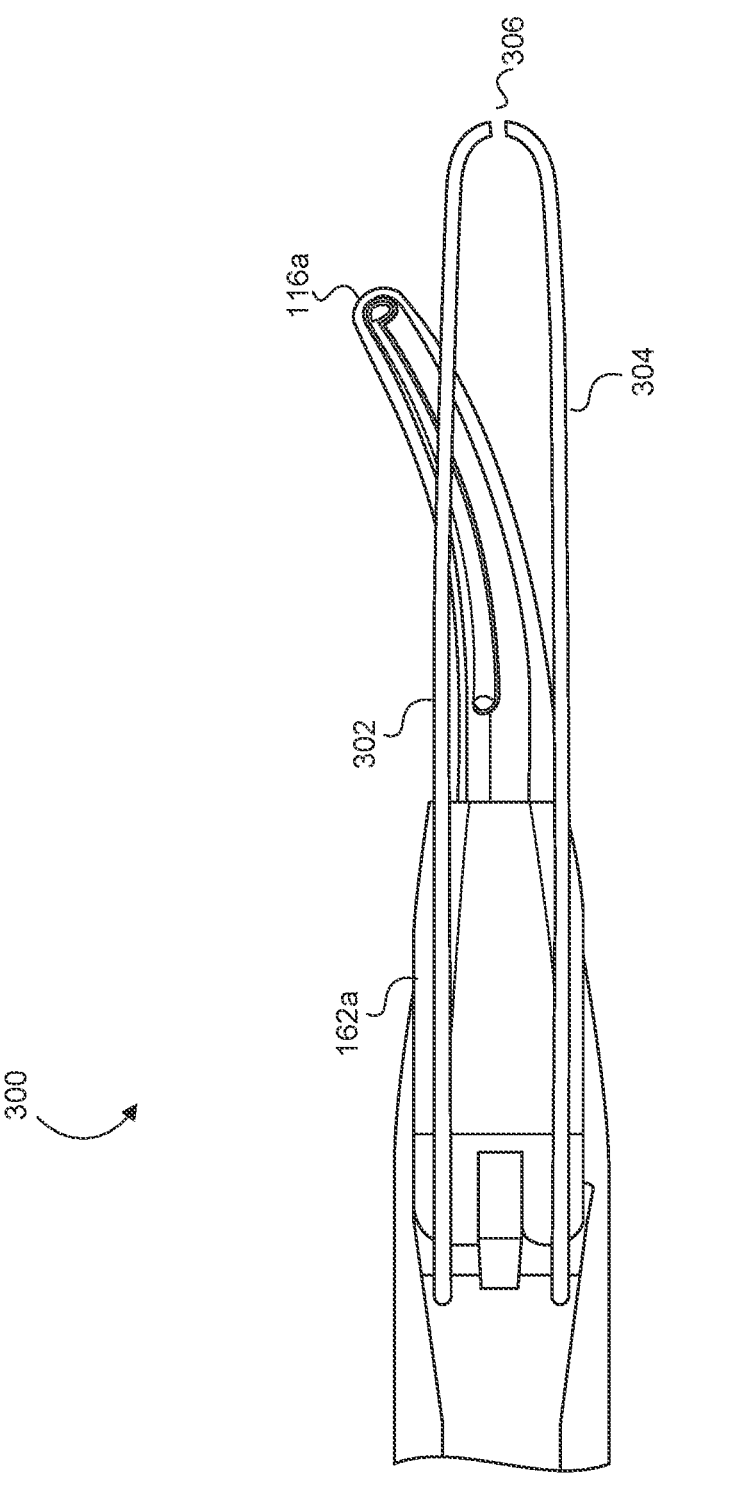
FIG. 3 shows an alternative design for including a nerve stimulation probe alongside the jaws of the surgical instrument, according to some aspects.

Referring to FIG. 3, illustration 300 shows an alternative design for including a nerve stimulation probe alongside jaws 116a and 116b, according to some aspects. Here, a retractable probe configuration in shown. Illustration 300 shows a portion of the medical device 100 from a top view perspective, here showing the top jaw 116a and corresponding jaw arm 162a. This configuration in the illustration 300 includes two retractable probes 302 and 304 that can extend beyond the distal end of the jaw 116a, as shown. The probes may be made of shape memory material so as to allow for the probes to be slightly modified in their design or shape, to be used as needed depending on the geometry of the surgical site. A gap 306 exists between the probes 302 and 304, such that the return path of the current may be completed if the ends of the probes 302 and 304 touch tissue. In this case, the second probe 304 acts as the return electrode. In other aspects, a single electrode may be supplied, and a subdermal needle or dispersive electrode in or nearby can act as the return electrode.

Figure 4:
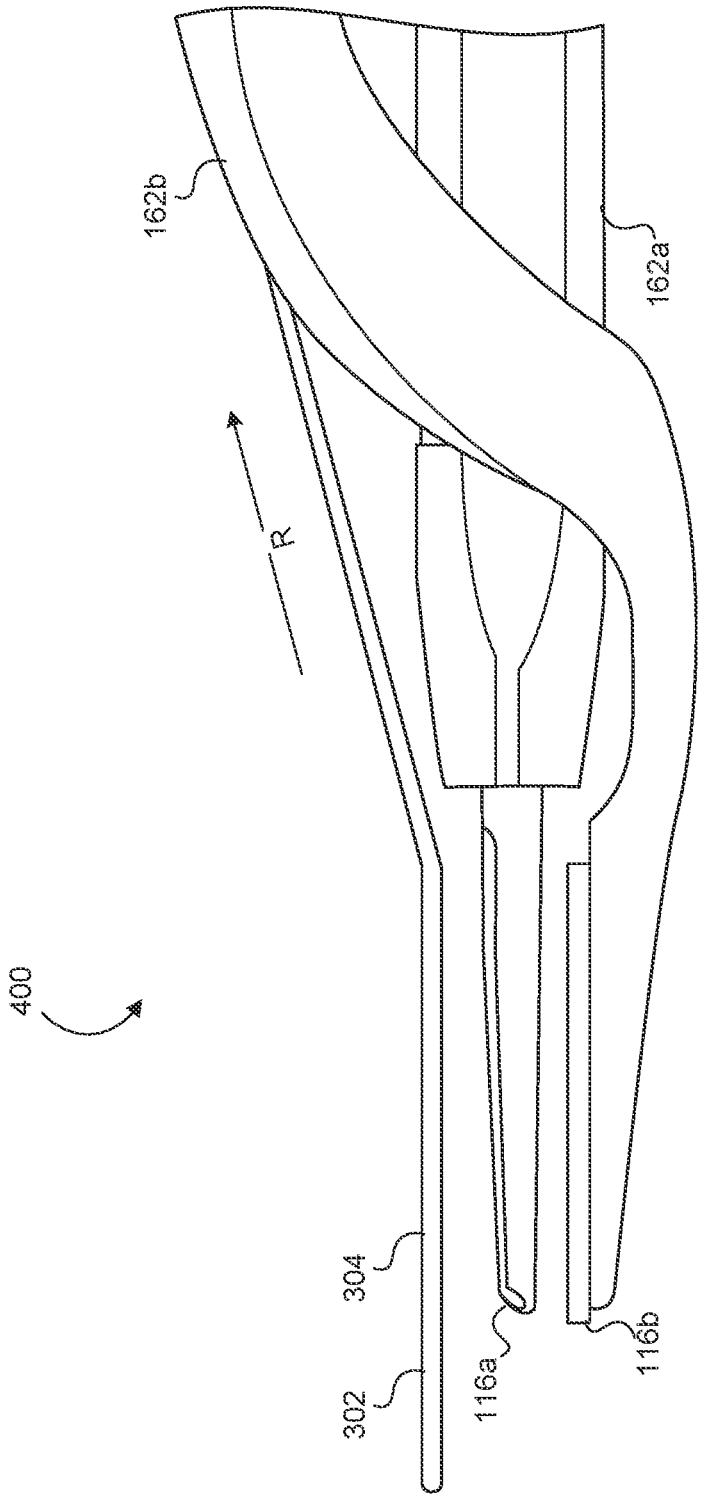
FIG. 4 shows a side view of the retractable probes, shown in FIG. 3.

Referring to FIG. 4, illustration 400 shows a side view of the retractable probes 302 and 304, shown in illustration 300. In this configuration, the probes 302 at 304 are located above the jaws 116a and 116b. In other cases, the probes may be located below the jaws or to the sides, and aspects are not so limited. From this view, it may be evident that the probes 302 and 304 may be retracted into the jaw arm 162b in direction R, as shown.

Figure 5:
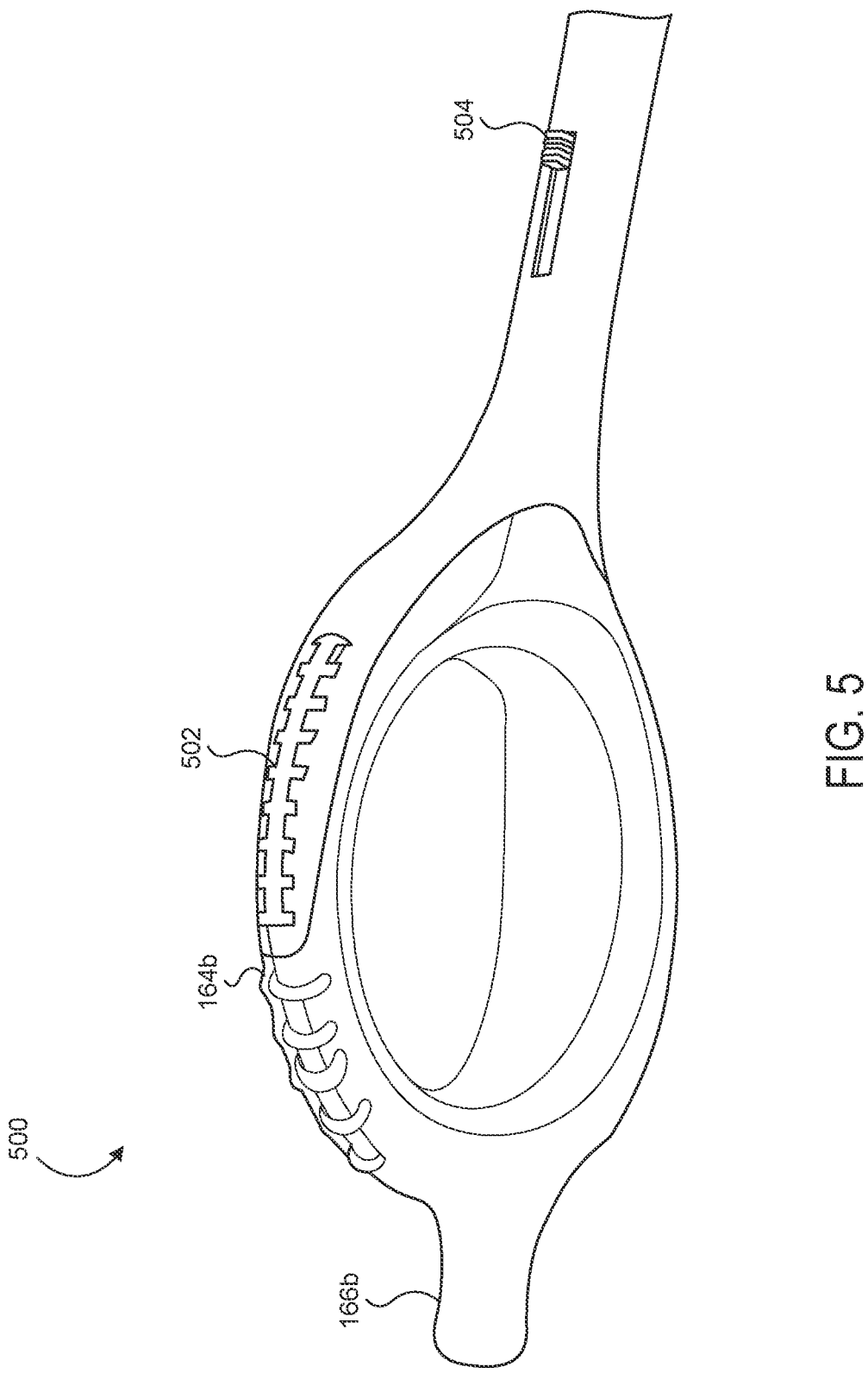
FIG. 5 shows portions of a retraction mechanism at the handle assembly to manipulate the retractable probes of FIGS. 3 and 4, according to some aspects.

Referring to FIG. 5, illustration 500 shows portions of a retraction mechanism to manipulate the retractable probes, shown in illustrations 300 and 400, according to some aspects. Here, a portion of the jaw handle 164b includes a slot 502 for a slide retraction mechanism to manipulate the retractable probes 302 and 304 (see FIG. 3). In this case, a knob or switch may be configured to slide back and forth within the slot 502 to retract and extend the probes 302 and 304. In other cases, the retractable probes may be manipulated through a wheel retraction mechanism, not shown. Regardless, the jaw handle 164b may include a current amplitude control switch 504 to control the level of current applied to the probes at the end effector.

Figure 6:
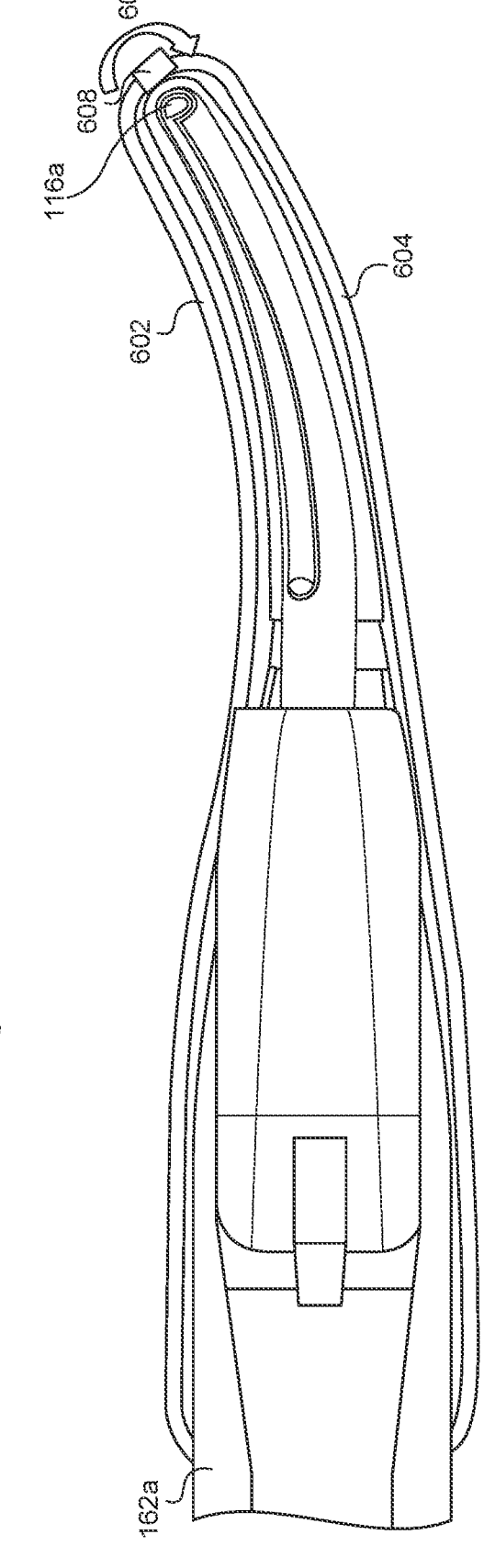
FIG. 6 shows another alternative design for including a nerve stimulation probe alongside the contours of the jaws of the surgical instrument, according to some aspects.

Referring to FIG. 6, illustration 600 shows another alternative design for including a nerve stimulation probe alongside the jaws 116a and 116b, according to some aspects. In this case, probes 602 and 604 are positioned around the perimeter of the jaw 116a and are shaped to follow the contours of the end effector. Illustration 600 shows this configuration from the top view of the medical device. Similar to the configuration in FIG. 3, the probes 602 and 604 are separated by a gap, in this case including a spacer 608 in that gap. Thus, spacer 608 may be secured to the distal end of the jaw 116b so as to stabilize the positions of the probes 602 and 604, or to otherwise prevent movement interference. The current path may again be closed once tissue touches both probes 602 and 604, where the current path travels in the direction of arrow 606. Thus, the probe 604 may act as the return electrode.

Figure 7:
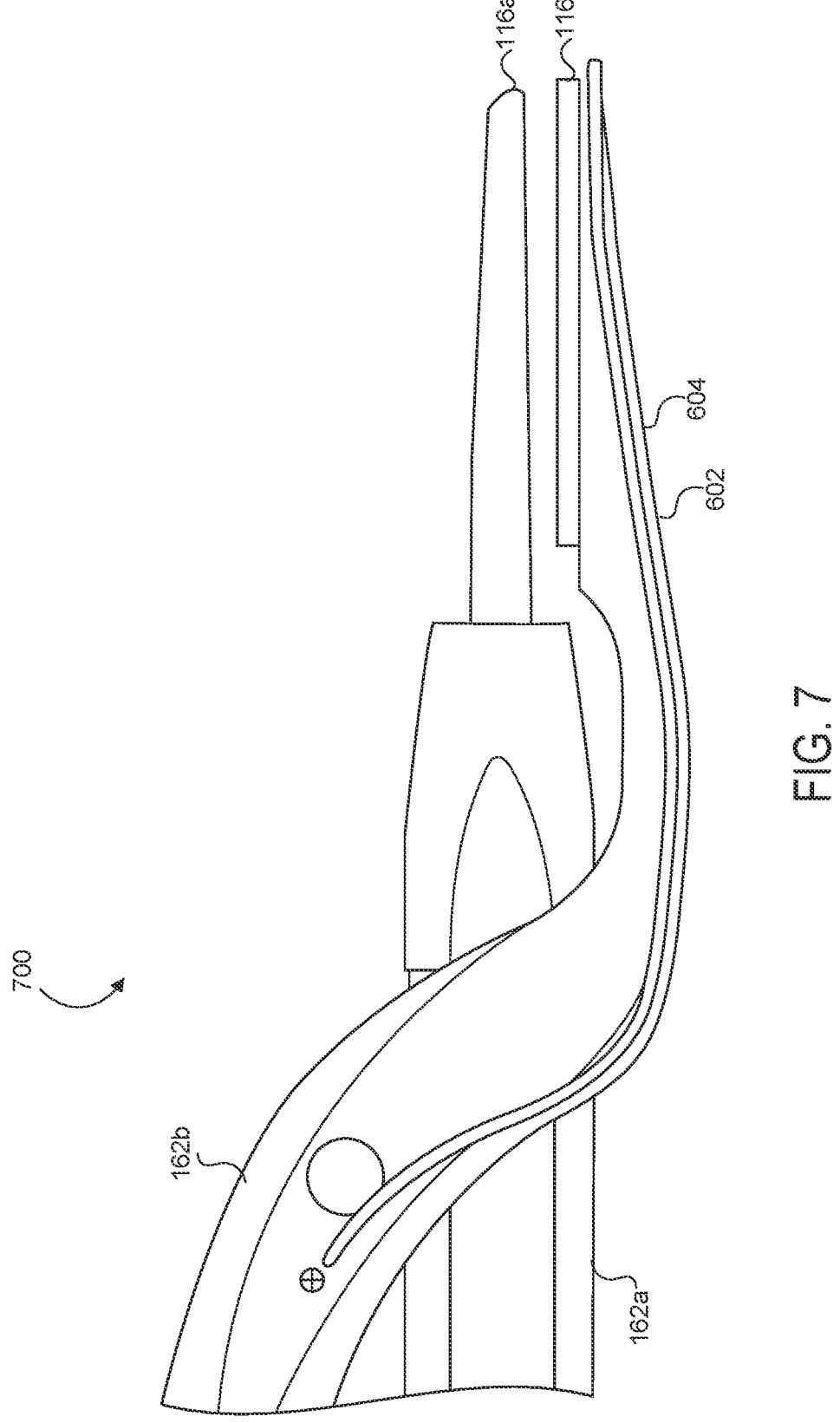
FIG. 7 shows the side view of the perimeter probes configuration of FIG. 6, according to some aspects.

Referring to FIG. 7, illustration 700 shows the side view of the perimeter probes configuration of illustration 600, according to some aspects. Here, the probes 602 and 604 are shown to be positioned on the perimeter of the jaw 116b and a portion of the jaw handle 162b. When combining the perspectives of illustrations 600 and 700, it may be apparent that the probes 602 and 604 follow the contours of the jaw perimeter. In this way, existing medical devices configured to supply therapeutic energy through the jaws may simply be repurposed or retrofitted to include a pair of electrodes or probes running along the perimeter of the jaws, to create a seamless and nonintrusive nerve stimulation feature.

Figure 8:
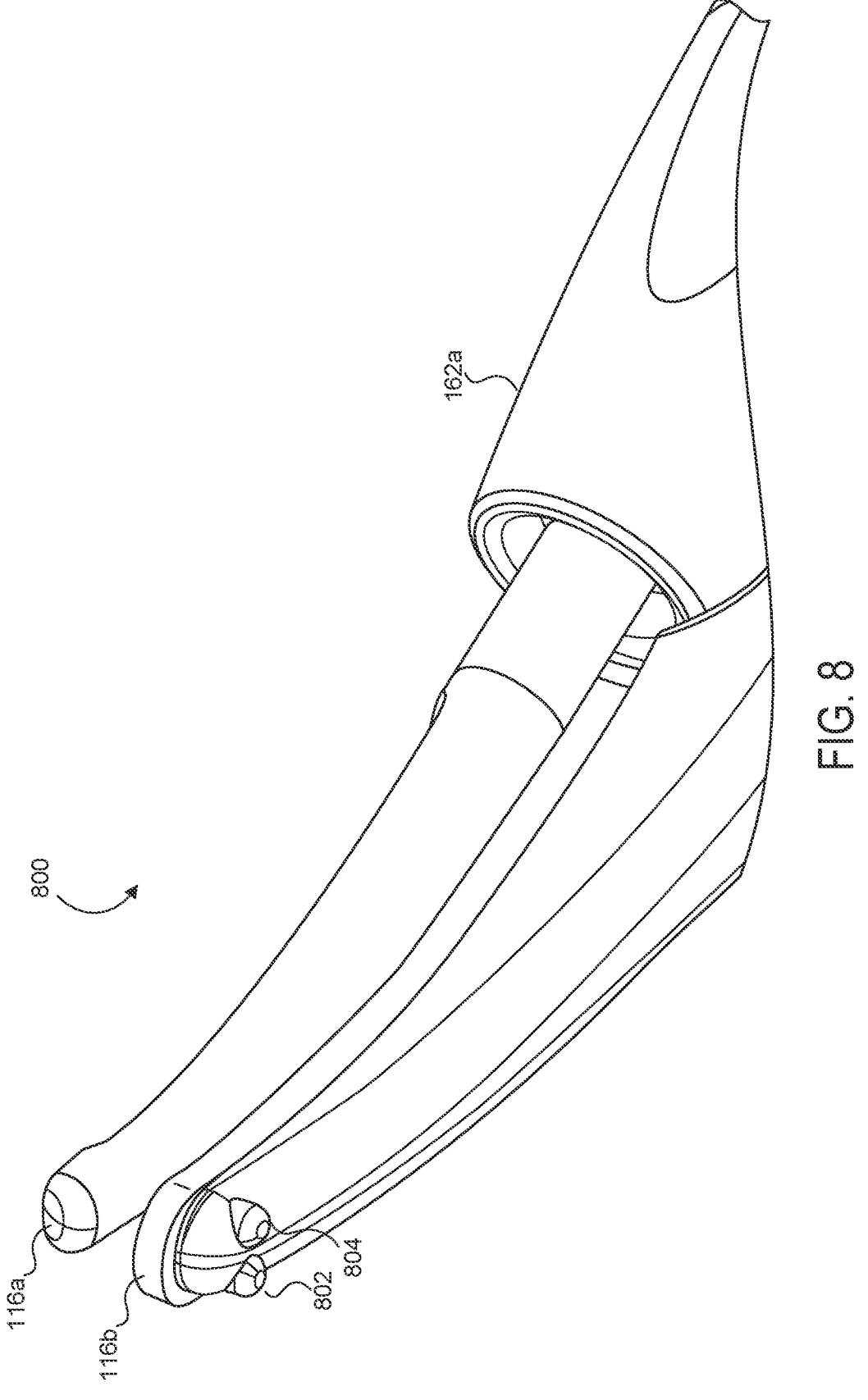
FIG. 8 shows yet another alternative design for including nerve stimulation at the jaws, including an electrical protrusion probe and return protrusion probe, according to some aspects.

Referring to FIG. 8, illustration 800 shows yet another alternative design for including nerve stimulation at the jaws 116a and 116b, according to some aspects. Here, two small electrode protrusions 802 and 804 at the distal end of the jaw 116b may be used for nerve stimulation and location. One of the protrusions may act as the stimulation probe while the other may act as the return electrode. The circuitry to reach the probes 802 and 804 may run through the jaw down to the distal end of the jaw 116b. While the probes 802 and 804 are shown and positioned on the outside and bottom of the jaw 116b, these probes may be positioned in other configurations. For example, the probes 802 and 804 may be positioned facing the front of the distal end of either jaw 116b or 116a. As another example, the probes 802 and 804 may be positioned on the top of the jaw 116a. In other cases, two sets of probes may be positioned at the distal end of the jaws, one pair on each of the jaws 116a and 116b.

Figure 9:
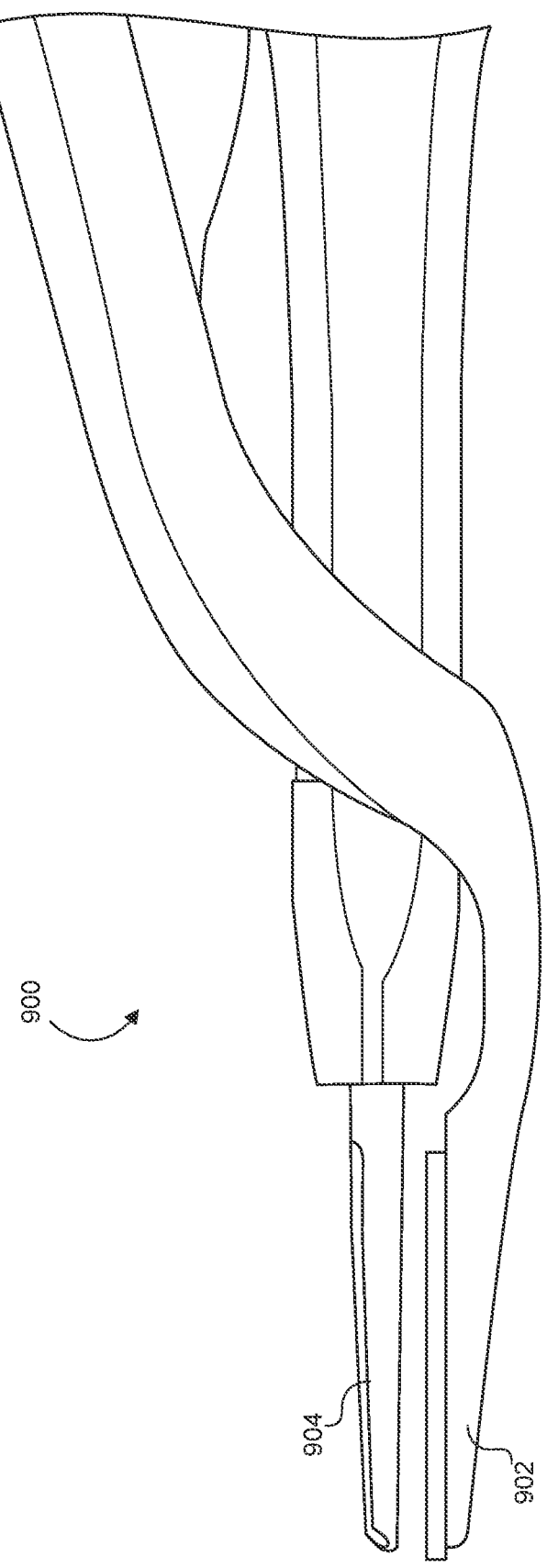
FIG. 9 shows yet another alternative design for including nerve stimulation in a surgical device, including enabling the blade to supply both therapeutic and nontherapeutic energy, according to some aspects.

Referring to FIG. 9, illustration 900 shows yet another alternative design for including nerve stimulation in a clamping medical device, according to some aspects. Here, one of the jaws 904 may serve as both a probe and a clamp and/or blade. That is, in one mode of the blade 904, therapeutic energy may be applied to perform various cutting or sealing procedures. In a second mode, the blade 904 may be activated to supply non-therapeutic energy in order to locate and/or stimulate nerves. In some cases, the clamping jaw 902 may act as a return electrode, while in other cases a subdermal needle or a dispersive electrode can act as the return electrode. In addition, it may be apparent that this alternative design in illustration 900 may be combined with the retractable probe, perimeter probe, or tip electrode configurations as discussed in FIGS. 3-8.

Figure 10:
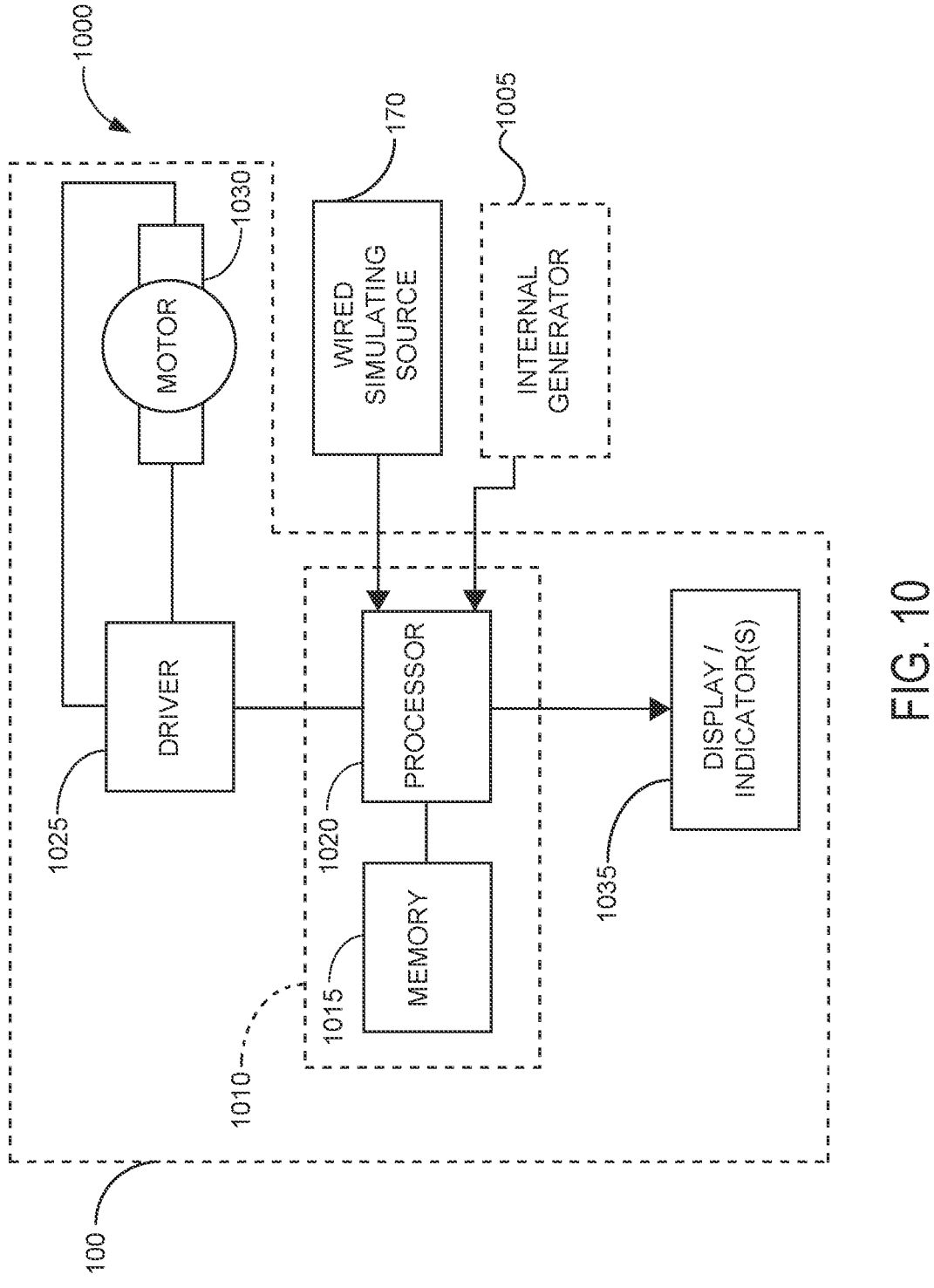
FIG. 10 is a block diagram of a surgical system comprising a grasping instrument with motor-driven components to apply energy to a surgical site, the surgical instrument coupled to a generator wired stimulating source (or alternatively having an internal generator), according to some aspects.

FIG. 10 is a block diagram of a surgical system 1000 comprising a grasping instrument 100 (FIG. 1) with motor-driven components to apply energy to a surgical site, the surgical instrument coupled to a generator wired stimulating source (or alternatively having an internal generator 1005), according to some aspects. The motor 1030 may be employed to close and open either one or both of the jaws 116a, 116b of the end effector 110 (FIG. 2) or firing the knife. Nevertheless, in most aspects, such functions would be hand-operated. The surgical system 1000 shows components of internal circuitry of the grasping instrument, and may also describe the internal circuitry of the alternative grasping instrument 200 (FIG. 2). The motor-driven surgical instrument 100 described in the present disclosure may be coupled to a wired stimulating source 170, such as a generator (or alternatively internal generator 1005) configured to supply power to the surgical instrument through external or internal means. While previous figures describe examples of the structures of the grasping, sealing, cutting, and probing components, FIG. 10 describes examples of the portions for how therapeutic and nontherapeutic energy may be delivered to the end effector. In certain instances, the motor-driven surgical instrument 100 may include a microcontroller 1010 coupled to an external wired generator 170 or internal generator 1005. Either the external generator 170 or the internal generator 1005 may be coupled to A/C mains or may be battery operated or combinations thereof. The electrical and electronic circuit elements associated with the motor-driven surgical instrument 100 and/or the generator elements 170, 1005 may be supported by a control circuit board assembly, for example. The microcontroller 1010 may generally comprise a memory 1015 and a microprocessor 1020 ("processor") operationally coupled to the memory 1015. The processor 1020 may control a motor driver 1025 circuit generally utilized to control the position and velocity of the motor 1030. The motor 1030 may be configured to control transmission of energy to the electrodes at the end effector of the surgical instrument. In certain instances, the processor 1020 can signal the motor driver 1025 to stop and/or disable the motor 1030, as described in greater detail below. In certain instances, the processor 1020 may control a separate motor override circuit which may comprise a motor override switch that can stop and/or disable the motor 1030 during operation of the surgical instrument in response to an override signal from the processor 1020. It should be understood that the term processor as used herein includes any suitable microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In some cases, the processor 1020 may be any single core or multicore processor such as those known under the trade name ARM Cortex by Texas Instruments. In some cases, any of the surgical instruments of the present disclosures may comprise a safety processor such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor may be configured specifically for IEC 61508 and ISO 26262 safety critical applications, among others, to provide advanced integrated safety features while delivering scalable performance, connectivity, and memory options.

In certain instances, the microcontroller 1010 may be an LM 4F230H5QR, available from Texas Instruments, for example. In at least one example, the Texas Instruments LM4F230H5QR is an ARM Cortex-M4F Processor Core comprising on-chip memory 1015 of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. Other microcontrollers may be readily substituted for use in the motor-driven surgical instrument 100. Accordingly, the present disclosure should not be limited in this context.

Referring again to FIG. 10, the surgical system 1000 may include a wired stimulating source 170, for example. In certain instances, the wired stimulating source 170 may be configured to supply power through external means, such as through electrical wire coupled to an external generator. In some cases, the surgical system 1000 also may include or alternatively include an internal generator 1005. The internal generator 1005 may be configured to supply power through internal means, such as through battery power or other stored capacitive source. Further descriptions of the internal generator 1005 and the wired generator 170 are described below.

In certain instances, the motor-driven surgical instrument 100 may comprise one or more embedded applications implemented as firmware, software, hardware, or any combination thereof. In certain instances, the motor-driven surgical instrument 100 may comprise various executable modules such as software, programs, data, drivers, and/or application program interfaces (APIs), for example. In certain instances, the surgical instrument 100 may also include one or more displays or other graphical indicators 1035, such as for indicating an energy level being applied to the end effector.

In some aspects, the return electrode may be double purposed to act as the electrical return for both therapeutic and nerve stimulation outputs. In this way, the delivery of the therapeutic energy may be in the form of monopolar electrosurgery, as the single return electrode may obviate the need for bipolar energy delivery. This configuration may be allowed in any of the examples showing a return electrode for the nerve stimulation energy path, including in FIGS. 1-10.

Figure 12:
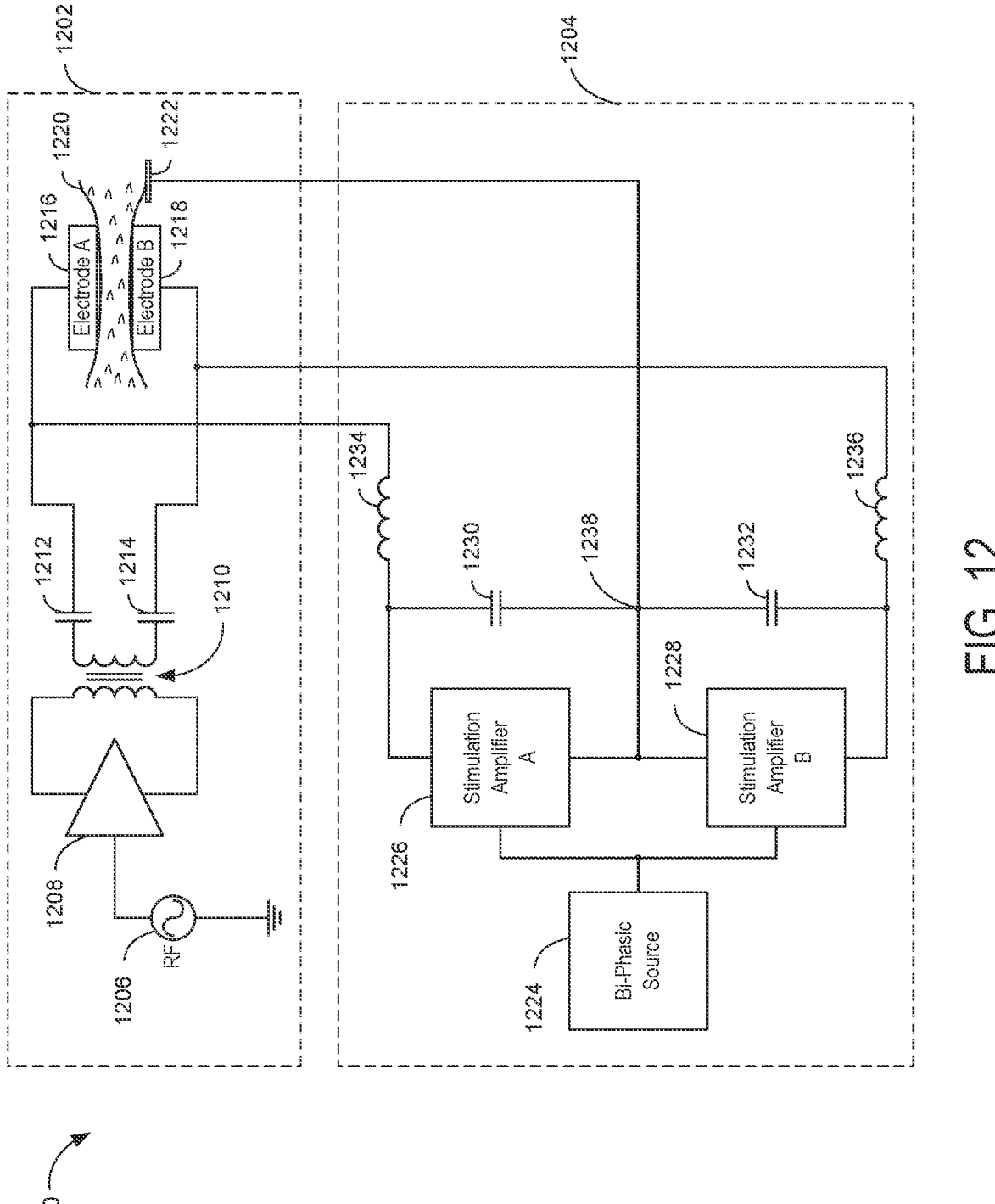
FIG. 12 illustrates one aspect of a nerve stimulation system 1200, according to some aspects.

FIG. 12 illustrates one aspect of a nerve stimulation system 1200, according to some aspects of the present disclosure. The nerve stimulation system 1200 provides a technique to stimulate nerves with a bipolar, ultrasonic, or a combination bipolar and ultrasonic instrument with multiple paths. The nerve stimulation system 1200 may represent one example of how the low energy stimulation may be combined with the high energy therapeutic applications in the same medical device, as described in FIGS. 1-11. Typically, a nerve stimulation electrode set is either a pair of closely-spaced electrodes or a probe electrode along with a return pad or needle. Tissue is placed between the first-described pair and stimulated, or the return pad or needle is placed in the appropriate position and then the target tissue is probed with the other electrode. In one aspect, the nerve stimulation system 1200 comprises two separate circuits, A and B, that are driven by the same waveform (preferably a biphasic source, but could be a simple direct current [DC] level). Both circuits A and B have a common return in the pad or needle, but A and B are configured to be out of phase with each other. In the case of a bipolar instrument, the A and B nodes are coupled to the treatment electrodes through an RF blocking circuit (low pass filter) such that the treatment RF is not conducted back through the stimulation circuit or through the needle or pad return of the stimulation circuitry. In this way, tissue can be stimulated between the treatment electrodes through the A and B circuits, and from A to the return or B to the return.

As shown with particularity in FIG. 12, the nerve stimulation system 1200 comprises an RF generator circuit 1202 and a nerve stimulation circuit 1204. The RF generator circuit 1202 comprises an RF source 1206 coupled to an amplifier 1208. The output of the amplifier 1208 is coupled to first and second blocking capacitors 1212, 1214 through an isolation transformer 1210. The first blocking capacitor 1212 is coupled to a first electrode 1216 and the second blocking capacitor 1214 is coupled to a second electrode 1220. As shown, tissue 1220 to be treated is located between the first and second electrodes 126, 1218. An electrically conductive element 1222, such as a pad or needle, is coupled to the tissue 1220 and to a common return 1238 of the nerve stimulation circuit 1204.

Turning now to the nerve stimulation circuit 1204, as shown in FIG. 12, the nerve stimulation circuit 1024 comprises a bi-phasic source 1224 coupled to two separate circuits, a first stimulation amplifier 1226 and a second stimulation amplifier 1228. As shown, the first and second stimulation amplifiers 1226, 1228 are driven by the same waveform, preferably generated by the biphasic source 1224, but they could be driven by a simple DC power source, for example. Both the a first and second stimulation amplifiers 1226, 1228 have a common return 1238 coupled to the tissue 1220 and can be coupled to a pad or needle. The first and second stimulation amplifiers 1226, 1228, however, are configured to be out of phase with each other. In the case of a bipolar instrument, the first and second stimulation amplifiers 1226, 1228 nodes are coupled to the treatment electrodes 1216, 1218 through corresponding RF blocking circuits (e.g., low pass filters), where the first blocking circuit comprises a first capacitor 1230 and a first inductor 1234 and the second blocking circuit comprises a second capacitor 1232 and a second inductor 1236 such that the treatment RF is not conducted back through the stimulation circuit 1204 or through the needle or pad 1222, which is coupled to the common return 1238 of the stimulation circuit 1204. In this way, the tissue 1220 can be stimulated between the treatment electrodes 1216, 1218 through the first and second amplifier circuits 1226, 1228, and from the first amplifier circuit 1226 to the return or from the second amplifier circuit 1228 to the return. Accordingly, first and second poles have separate signal generation circuits comprising first and second amplifier circuits 1226, 1228 with a common return 1238. The path for stimulation can be either through the first amplifier circuit 1226 or through the second amplifier circuit 1228 to the return 1238 as well as from the first amplifier circuit 1226 to the second amplifier circuit 1228 due to the common return 1238.

A combination RF and ultrasonic instrument can be configured to deliver RF energy, ultrasound energy, and can stimulate nerves all in the same instrument/generator. Advantages include, without limitation, simplicity for the surgeon, reduced need for instrument exchange, incorporating the nerve stimulation function within the jaws of the instrument such that tissue can be evaluated for nerves before the full force of grasping is applied to the tissue (avoiding damage to those nerve or structure) and before applying energy destroying the nerves that may be in the grasp of the instrument or treated with the thermal effects of the RF and/or Ultrasound therapeutic energy.

In other aspects, the therapeutic energy treatment may comprise laser, microwave, among other energy sources.

In other aspects, nerve stimulation signals can be generated within the generator either via separate circuits in the handle of the device or with a special output waveform from the generator.

Further, in other aspects, a nerve stimulation signal may be applied between the treatment electrodes automatically prior to the jaws being fully closed so the surgeon can observe any stimulation effect and potentially avoid unwanted nerve damage. In one aspect, a controller may be employed to shut off this function. In another aspect, an indicator may be located on the instrument to show that the nerve stimulation circuit is "on," e.g., energized, activated, etc., as shown in IEC 60601-2-10, which shows indicators for such stimulation instruments.

In other aspects, a tissue sensing circuit is proved that turns "on," e.g., energizes, activates, etc., the nerve stimulation signal when tissue is in contact with the stimulation electrodes or the therapeutic electrodes, or ultrasonic blade, or tissue pad.

The energy profile of the nerve stimulation functionality of the present disclosures differs from the energy profiles of the therapeutic functionalities. Aspects of the present disclosures therefore include a description of how nerve stimulation energy may be generated alongside therapeutic energy generation.

In some cases, various aspects may be implemented as an article of manufacture. The article of manufacture may include a computer readable storage medium arranged to store logic, instructions and/or data for performing various operations of one or more aspects. In various aspects, for example, the article of manufacture may comprise a magnetic disk, optical disk, flash memory or firmware containing computer program instructions suitable for execution by a general purpose processor or application specific processor. The aspects, however, are not limited in this context.

The functions of the various functional elements, logical blocks, modules, and circuits elements described in connection with the aspects disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures, and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some aspects also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the aspects described herein illustrate example implementations, and that the functional elements, logical blocks, modules, and circuits elements may be implemented in various other ways which are consistent with the described aspects. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual aspects described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA, or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers, or other such information storage, transmission, or display devices.

It is worthy to note that some aspects may be described using the expression "coupled" and "connected" along with their derivatives. These terms are not intended as synonyms for each other. For example, some aspects may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, and application program interface, exchanging messages, and so forth.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

The invention claimed is:

1. A method of operating a surgical instrument, the method comprising:
moving (i) a first jaw coupled to a distal end of a first jaw arm and (ii) a second jaw coupled to a distal end of a second jaw arm of the surgical instrument from an open configuration to a closed configuration to capture tissue positioned between the first jaw and the second jaw, wherein a proximal end of the first jaw arm is coupled to a first jaw handle and a proximal end of the second jaw arm is coupled to a second jaw handle, and wherein moving the first and second jaws comprises rotating each of the first and second jaws about a pivot joint located between the respective distal and proximal ends;
energizing an electrode of the surgical instrument to deliver a first energy to tissue positioned between the first jaw and the second jaw;
moving a probe of the surgical instrument from a retracted configuration in which the probe is retracted into a housing of the first jaw arm or a housing of the second jaw arm to an extended configuration; and
energizing the probe to deliver a second energy to the tissue.

2. The method of claim 1, wherein the second energy comprises nontherapeutic energy for providing electrical stimulation to the tissue.

3. The method of claim 1, wherein moving the probe of the surgical instrument from the retracted configuration to the extended configuration comprises:
moving a first probe of the surgical instrument from a retracted configuration in which the first probe is retracted into the housing of the first jaw arm or the housing of the second jaw arm to an extended configuration, and
moving a second probe of the surgical instrument from a retracted configuration in which the second probe is retracted into the housing of the first jaw arm or the housing of the second jaw arm to an extended configuration.

4. The method of claim 3, wherein moving the first probe and moving the second probe comprises moving the first probe and the second probe to define a gap between a distal end of the first probe and a distal end of the second probe.

5. The method of claim 3, wherein moving the first probe and moving the second probe comprises moving the first probe and the second probe to define a gap between a distal end of the first probe that is contoured toward the gap and a distal end of the second probe that is contoured toward the gap.

6. The method of claim 1, wherein moving the probe of the surgical instrument comprises moving a probe of the surgical instrument that is positioned adjacent the first jaw and the second jaw.

7. The method of claim 1, wherein moving the probe of the surgical instrument comprises operating a retraction mechanism of the surgical instrument to move the probe between the extended configuration and the retracted configuration.

8. The method of claim 7, wherein operating the retraction mechanism comprises operating a wheel retraction mechanism.

9. The method of claim 7, wherein operating the retraction mechanism comprises operating a slide retraction mechanism.

10. The method of claim 1, wherein moving the probe of the surgical instrument comprises moving a probe formed from a shape memory material.

11. The method of claim 1, wherein energizing the probe comprises operating a switch to control an amount of the second energy delivered to the probe from an energy source.

12. The method of claim 1, wherein energizing the electrode of the surgical instrument to deliver the first energy to tissue positioned between the first jaw and the second jaw comprises energizing the electrode of the surgical instrument to deliver therapeutic energy to the tissue configured for sealing or cutting of the tissue.

13. A nerve stimulation system of a surgical instrument, the nerve stimulation system comprising: a radio frequency (RF) generator circuit including an RF source, a first electrode, a second electrode, and a first amplifier electrically coupled to the RF source and each of the first and second electrodes; and a nerve stimulation circuit including a bi-phasic source, a second amplifier, and a third amplifier, wherein each of the second and third amplifiers is electrically coupled to the bi-phasic source, further wherein the second amplifier and the third amplifier are out of phase relative to each other.

14. The nerve stimulation system of claim 13, wherein the second amplifier is electrically coupled to the first electrode of the RF generator circuit and wherein the third amplifier is electrically coupled to the second electrode of the RF generator circuit.

15. The nerve stimulation system of claim 13, wherein the RF generator circuit further includes an electrically conductive element, and wherein each of the second and third amplifier is electrically coupled to the electrically conductive element.

16. The nerve stimulation system of claim 15, wherein the electrically conductive element comprises a electrically conductive pad.

17. The nerve stimulation system of claim 15, wherein the electrically conductive element comprises a electrically conductive needle.

18. The nerve stimulation system of claim 13, wherein the RF generator circuit further comprises an isolation transformer electrically coupled to the first amplifier, a first blocking capacitor electrically coupled to the isolation transformer and the first electrode, and a second blocking capacitor electrically coupled to the isolation transformer and to the second electrode.

19. The nerve stimulation system of claim 13, wherein the nerve stimulation circuit further comprises (i) a first RF blocking circuit electrically coupled to the second amplifier and to the first electrode of the RF generator circuit and (ii) a second RF blocking circuit electrically coupled to the third amplifier and to the second electrode of the RF generator circuit.

* * * * *